US011234607B2

(12) United States Patent
Barlow et al.

(10) Patent No.: US 11,234,607 B2
(45) Date of Patent: Feb. 1, 2022

(54) METHODS OF USING AN ENHANCED THERAPEUTIC STIMULUS FOR NON-NUTRITIVE SUCK ENTRAINMENT SYSTEM

(75) Inventors: Steven M. Barlow, Lawrence, KS (US); David L. Stalling, Shawnee, KS (US); Kenneth Aron, Shawnee, KS (US)

(73) Assignees: Innara Health, Inc., Olathe, KS (US); University of Kansas, Lawrence, KS (US)

( * ) Notice: Subject to any disclaimer, the term of this patent is extended or adjusted under 35 U.S.C. 154(b) by 1235 days.

(21) Appl. No.: 13/457,154

(22) Filed: Apr. 26, 2012

(65) Prior Publication Data

US 2012/0209147 A1 Aug. 16, 2012

Related U.S. Application Data

(63) Continuation-in-part of application No. 12/390,142, filed on Feb. 20, 2009, now Pat. No. 8,226,579.

(Continued)

(51) Int. Cl.
*A61B 5/03* (2006.01)
*A61B 5/00* (2006.01)

(52) U.S. Cl.
CPC .............. *A61B 5/038* (2013.01); *A61B 5/486* (2013.01); *A61B 5/682* (2013.01); *A61B 5/6896* (2013.01)

(58) Field of Classification Search
CPC .......... A61B 5/038; A61B 5/682; A61B 5/486
See application file for complete search history.

(56) References Cited

U.S. PATENT DOCUMENTS 4,232,687 A 11/1980 Anderson-Shanklin
5,309,919 A * 5/1994 Snell ................... A61N 1/37247
600/510

(Continued)

FOREIGN PATENT DOCUMENTS

CN 101080195 B1 11/2012
EP 1786319 B1 10/2012

(Continued)

OTHER PUBLICATIONS

Goldfield et al.; "Coordination of Sucking, Swallowing, and Breathing and Oxygen Saturation During Early Infant Breast-feeding and Bottle-feeding"; Pediatric Research; vol. 60; No. 4; pp. 450-455; Oct. 2006.

(Continued)

*Primary Examiner* — Devin B Henson
*Assistant Examiner* — H. Q. Nguyen
(74) *Attorney, Agent, or Firm* — Polsinelli PC

(57) ABSTRACT

The present invention relates to methods of using a therapeutic system. In particular, the present invention relates to procedures and methods of using a system having hardware, software, and appliance components for assessing and entraining a non-nutritive suck (NNS) pattern in a patient. The methods include configuring the hardware and software systems to receive data from an orofacial stimulation appliance and to generate a precise therapeutic pulse profile that is actuated as a tactile stimulus. The methods also include collecting data using the orofacial stimulation appliance and delivering the tactile stimulus via the orofacial stimulation appliance to entrain an organized NNS pattern.

12 Claims, 23 Drawing Sheets

Related U.S. Application Data

(60) Provisional application No. 61/036,304, filed on Mar. 13, 2008, provisional application No. 61/030,484, filed on Feb. 21, 2008.

(56) References Cited

U.S. PATENT DOCUMENTS

| | | | |
|---|---|---|---|
| 5,435,304 A * | 7/1995 | Oppelt | A61B 17/2258 600/439 |
| 5,830,235 A | 11/1998 | Standley | |
| 6,033,367 A | 3/2000 | Goldfield | |
| 7,435,232 B2 | 10/2008 | Liebschner | |
| 7,917,201 B2 | 3/2011 | Gozani et al. | |
| 8,157,731 B2 | 4/2012 | Teller et al. | |
| 8,226,579 B2 | 7/2012 | Barlow et al. | |
| 8,251,926 B2 | 8/2012 | Barlow et al. | |
| 2003/0216944 A1 * | 11/2003 | Stavis | G16H 15/00 705/3 |
| 2004/0019382 A1 | 1/2004 | Amirouche et al. | |
| 2004/0128163 A1 * | 7/2004 | Goodman | G06F 19/3406 705/2 |
| 2006/0074354 A1 | 4/2006 | Barlow et al. | |
| 2006/0079814 A1 | 4/2006 | Barlow et al. | |
| 2007/0182571 A1 * | 8/2007 | Kennish | G09B 19/0076 340/573.1 |
| 2008/0013100 A1 * | 1/2008 | Chang | G01B 11/2441 356/511 |
| 2009/0156967 A1 | 6/2009 | Cohen | |
| 2009/0222214 A1 | 9/2009 | Barlow et al. | |
| 2010/0016675 A1 * | 1/2010 | Cohen | A61B 5/6896 600/300 |
| 2010/0075285 A1 | 3/2010 | Stalling et al. | |
| 2011/0060252 A1 | 3/2011 | Simonsen et al. | |

FOREIGN PATENT DOCUMENTS

| | | |
|---|---|---|
| GB | 1206014 A | 9/1970 |
| WO | 2006026623 A2 | 3/2006 |
| WO | 2006081376 A1 | 8/2006 |
| WO | 2008067607 A1 | 6/2008 |

OTHER PUBLICATIONS

Vantipali et al.; Somatosensory entrainment of suck in preterm infants: NTrainer CNL Technical Research Report, 2006; 3:1-23.
PCT/US2013/038405 International Search Report and Written Opinion dated Jul. 11, 2013 (10 pages).
PCT/US2013/038410 International Search Report and Written Opinion dated Jul. 15, 2013 (8 pages).
Barlow et al, "Synthetic orocutaneous stimulation entrains preterm infants with feeding difficulties to suck." J Perinatol, 2008, pp. 541-548, vol. 28, No. 8.
Barlow et al, "Mechanically evoked perioral reflexes in infants." Brain Res., 1992, pp. 158-160, vol. 599, No. 1.
Finan et al., "The actifier: a device for neurophysiological studies of orofacial control in human infants." J Speech Hear Res, 1996, pp. 833-838, vol. 39, No. 4.
Chinese Applicaiton Serial No. 200910008046.7, Response filed Apr. 28, 2012 to Office Action dated Dec. 13, 2011, 4 pgs.
Chinese Application Serial No. 200910008046.7, Office Action dated Dec. 13, 2011, 5 pgs.
European Application Serial No. 09250464.6, Office Action dated Mar. 22, 2012, 11 pgs.
Estep et al., "Non-Nutritive Suck Parameter in Preterm Infants with RDS." J Neonatal Nurs, 2008, pp. 28-34, vol. 14, No. 1.
Poore et al., "Respiratory treatment history predicts suck pattern stability in preterm infants." J Neonatal Nurs, 2008, pp. 185-192, vol. 14, No. 6.
Popescu et al., "Non-nutritive sucking recorded in utero via fetal magnetography." Physiol Meas, 2008, pp. 127-139, vol. 29, No. 1.
Stumm et al., "Respiratory Distress Syndrome Degrades the Fine Structure of the Non-Nutritive Suck in Preterm Infants." J Neonatal Nurs, 2008, pp. 9-16, vol. 14, No. 1.
PCT/US13/38400 International Search Report and Written Opinion dated Jul. 19, 2013 (15 pages).
Poore et al., "Patterned orocutaneous therapy improves sucking and oral feeding in preterm infants", Acta Paediatrica, vol. 97, No. 7, Jul. 1, 2008, pp. 920-927, ISSN: 083-5253, DOI: 10.1111/j.1651-2227.2008.00825.x.

* cited by examiner

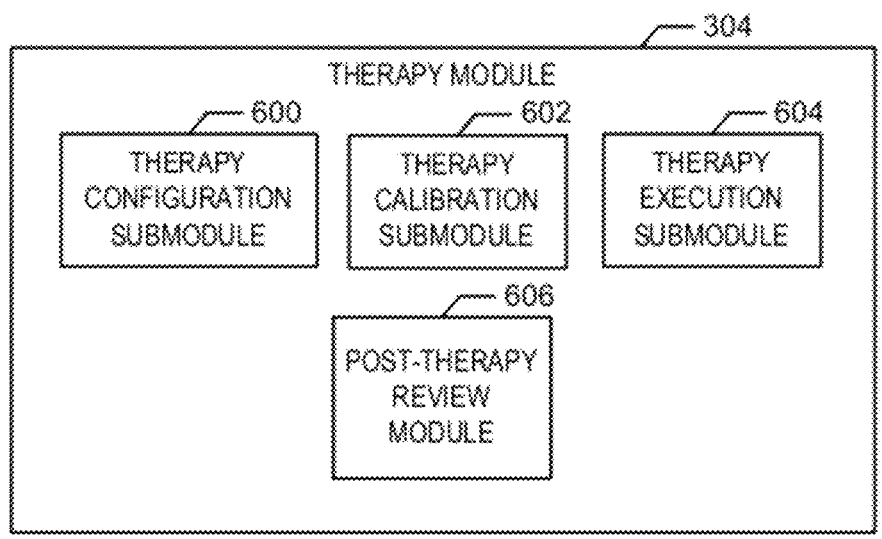
FIG. 6
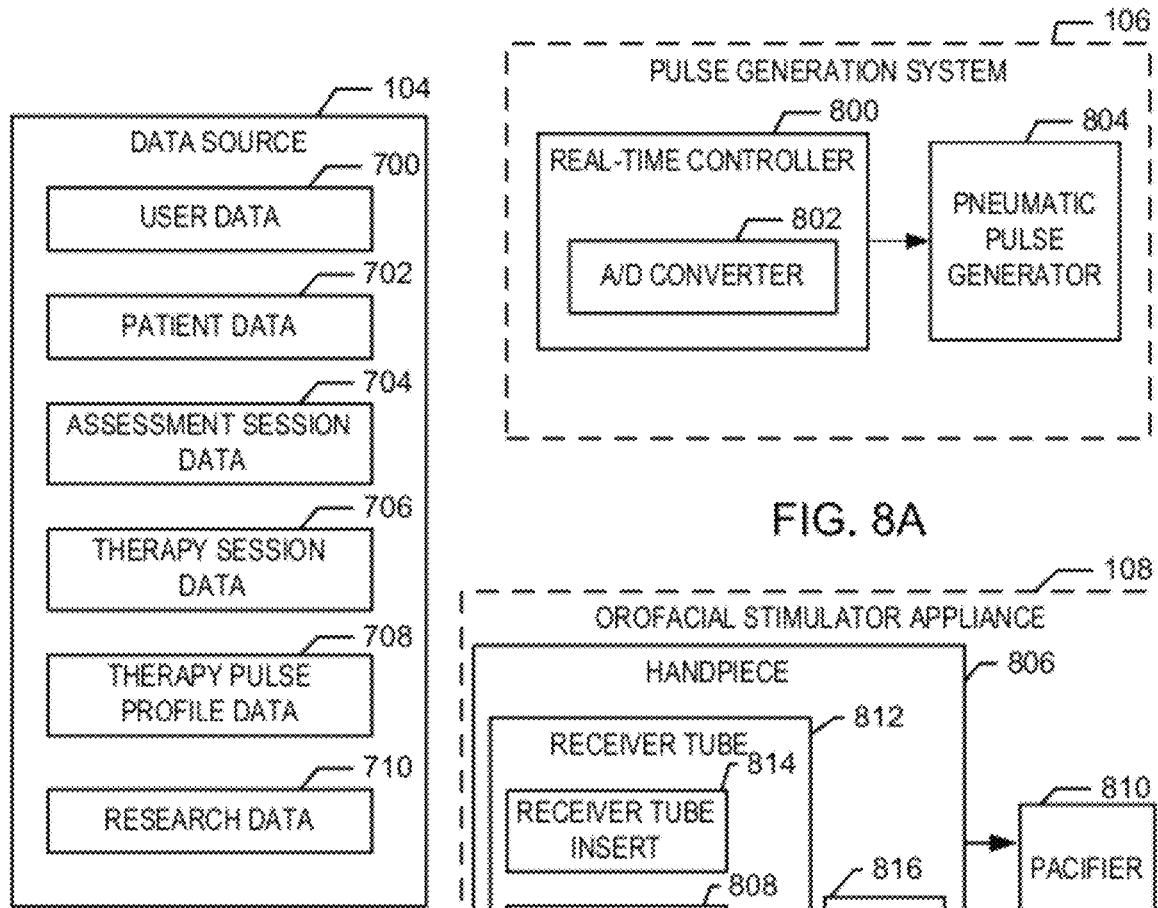
FIG. 7
FIG. 8A
FIG. 8B

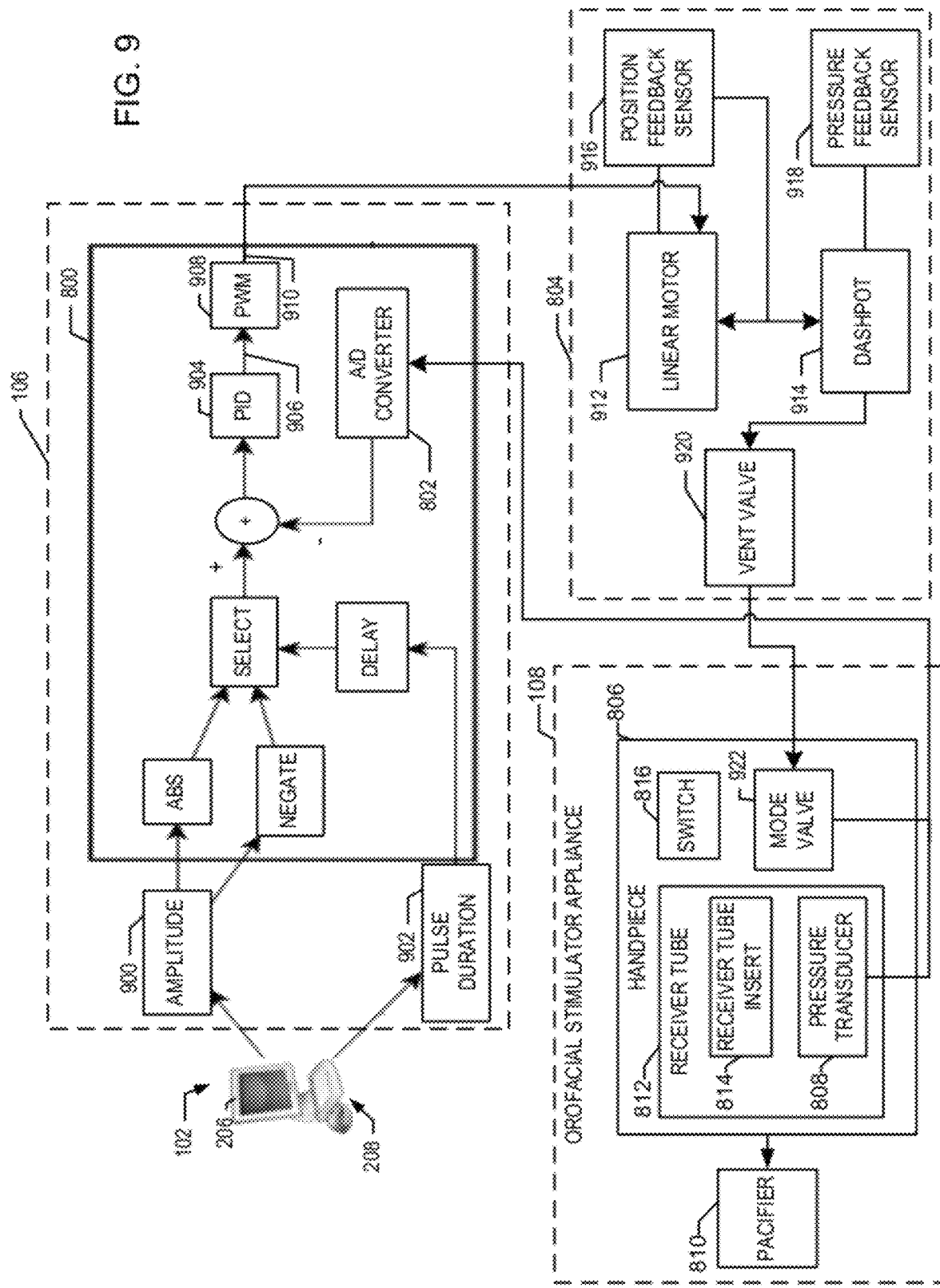

Adding New Patient

Background

Last | First | Middle | Patient Alias

Hospital ID | Birthdate 11/11/1111 | CA at Birth __ weeks __ days

Primary Clinician <unknown> | Weight (grams) | Gender ○ Male ○ Female

Assessment Schedule
 0 Assessments / week
 0 Number of weeks
 0 Number of sessions Therapy Schedule
 0 Therapies / day
 0 Number of weeks
 0 Number of sessions (Cancel) (Save)

Configuring Assessment

Patient: Van Houten, Milhouse R.

Chime with prompt ☑ — 1230 — 1244
Prompt me after (min): 3 — 1232 — 1246
Stop after (min): 3 — 1234
Installed Pacifier: No Value — 1236
1238 — ☐ Scented Pacifier
Patient Weight (grams): ⸺ 1248

Cancel — 1240   Continue... — 1242

Please describe the dominant patient state for the session

Patient State: No Value

Please verify that the completed assessment is assigned to the correct patient

⦿ correct, assigned to patient: Simpson, Homer
◯ incorrect, reassign to patient

Add optional notes

METHODS OF USING AN ENHANCED THERAPEUTIC STIMULUS FOR NON-NUTRITIVE SUCK ENTRAINMENT SYSTEM

CROSS REFERENCE TO RELATED APPLICATIONS

This application is a continuation-in-part of U.S. patent application Ser. No. 12/390,142, entitled "Method and Apparatus for Measuring Non-Nutritive Suck Pattern Stability" filed on Feb. 20, 2009, which claims priority to U.S. Provisional Application No. 61/036,304 filed on Mar. 13, 2008 and U.S. Provisional Application No. 61/030,484 filed on Feb. 21, 2008, all of which are incorporated by reference in their entireties.

FEDERALLY SPONSORED RESEARCH OR DEVELOPMENT

The subject matter discussed in this patent application was funded in part by United States Grant No. R01-DC003311 from the National Institute of Health (NIH). The government may have certain rights to the subject matter discussed herein.

FIELD OF THE INVENTION

The invention relates generally to methods and procedures using hardware and software systems, including any processing devices or appliances incorporating the software system to assess the organization of a non-nutritive suck (NNS) pattern of a patient and to entrain an organized NNS pattern in the patient. More specifically, the present invention relates to methods of monitoring and administering tactile stimuli to assess the patient's natural NNS pattern and to entrain an organized NNS pattern.

BACKGROUND OF THE INVENTION

Premature birth places infants at increased risk for learning disabilities, delayed development of speech, language and motor skills, and mortality. The premature infant often has difficulties with respiration and feeding and therefore may remain in the hospital for prolonged periods of time. The non-nutritive suck (NNS) is a motor behavior that can be observed and used to make inference about brain development and organization in this young population.

Oral stimulation therapy is a common practice, in which feeding therapists manually apply a stimulation using their fingertip. Manually applying stimulation, however, has a number of drawbacks. One such drawback includes the variance and limitation in the amount of motion (amplitude) and rhythm (frequency) from therapist to therapist, or even by the same individual. As a result, extensive and costly training and experience are required for a therapist to be proficient at providing manual stimulation and assessment.

In addition, manual stimulation is given essentially blind, as patients can respond by producing a variety of undesirable motor actions, including but not limited to clenching the jaws, tongue compression, tongue thrusting, or other reactions that may be confused with desirable NNS events. As such, it can be difficult to determine if the manual stimulation is beneficial to the patient.

Therefore, a need exists for an automated system and method of using the system to assess a patient's natural NNS pattern and to provide precise and beneficial tactile stimulus to correct and organize the patients NNS pattern.

SUMMARY OF THE INVENTION

The present invention relates to a method of using a system having hardware, software, and appliance components for assessing and entraining a non-nutritive suck (NNS) pattern in a patient. In one aspect, a method is performed using a non-nutritive suck appliance assembly in communication with a non-nutritive suck application system to assess a non-nutritive suck pattern of patient. The method includes steps performed at a user interface generated for display on a display device of the non-nutritive suck application system. The steps include selecting the patient's name from a displayed list of patients generated by the non-nutritive suck application system, the non-nutritive suck application system having memory and executing a non-nutritive suck application on at least one processor. The steps also include selecting an assessment mode of the non-nutritive suck application, selecting a displayed "new assessment" control button, selecting an assessment to be performed at the user interface and configuring the assessment at the user interface.

The method also includes steps for calibrating an orofacial stimulator appliance of the non-nutritive suck appliance assembly to perform the selected assessment procedure. The method further includes the steps of positioning the patient to encourage a rooting response to the orofacial stimulator appliance, starting the assessment, and inserting the orofacial stimulator appliance into the patient's mouth. The orofacial stimulator appliance is held to maintain contact with the patient's mouth during the assessment, and then removed from the patient's mouth at the conclusion of the assessment session. The method also includes providing summary remarks regarding the assessment at the user interface.

In another aspect, a method is performed using a non-nutritive suck appliance assembly in communication with a non-nutritive suck application system to entrain a non-nutritive suck pattern of a patient. The method includes steps performed at a user interface generated for display on a display device of the non-nutritive suck application system. The steps include selecting the patient's name from a displayed list of patients generated by the non-nutritive suck application system, the non-nutritive suck application system having memory and executing a non-nutritive suck application on at least one processor. The steps also include selecting a therapy mode of the non-nutritive suck application, selecting a displayed "new therapy" control button, and, configuring a therapy protocol to be performed.

The method also includes steps for calibrating an orofacial stimulator appliance of the non-nutritive suck appliance assembly to perform the selected therapy protocol. The method further includes the steps of positioning the patient to encourage a rooting response to the orofacial stimulator appliance, starting the selected therapy protocol, and inserting the orofacial stimulator appliance into the patient's mouth. The orofacial stimulator appliance is held to maintain contact with the patient's mouth during the therapy protocol, and then removed from the patient's mouth at the conclusion of the therapy protocol. The method also includes providing summary remarks regarding the therapy protocol at the user interface.

In yet another aspect, a method is performed using a non-nutritive suck appliance assembly in communication with a non-nutritive suck application system to generate a productive non-nutritive suck pattern in a patient. The method includes assessing a current non-nutritive suck pattern of the patient, as described herein, reviewing an assessment waveform received by the non-nutritive suck application from the orofacial stimulator appliance, determining if a therapy protocol is necessary to generate the productive non-nutritive suck pattern, and providing a therapeutic stimulus to the patient, as described herein.

In other aspects, the method further includes administering a therapy protocol by using the hardware, software, and appliance components to generate a therapeutic pressure pulse signal comprising a base frequency signal further comprising two or more pressure pulses, wherein each pulse period consists of a positive and negative displacement contacted by the lip and the mouth of the patient. Pulses are administered in a series of two or more pulses, and each of the two or more pressure pulses has a damped harmonic oscillating square wave profile and are separated by an interval between 500 milliseconds and 650 milliseconds in duration. The method may also include generating a therapeutic pressure profile signal comprising at least one of the therapeutic pressure pulse signals and transmits the therapeutic pressure pulse profile signal to the orofacial stimulator appliance.

In various aspects, the base frequency is between 1.5 Hz and 5 Hz and the two or more pressure pulses causes surface motion of between about 260 microns and 300 microns, with a maximum transition interval of 20 milliseconds to 50 milliseconds. The therapeutic pressure profile may include at least six pressure pulses in succession contacted with the patient for at least two minutes, at least twice a day. Further, each of the two or more pressure pulse is composed of higher order harmonics of the base frequency and each pressure pulse has a square wave peak.

In various aspects, the methods further comprise calibrating the orofacial stimulator appliance by mounting a pacifier onto an end of the orofacial stimulator appliance or optionally, inserting a therapy insert into a receiver tube of the orofacial stimulator appliance. In addition, the calibration of the orofacial stimulator appliance, as well as the expansion characteristics of the pacifier may be verified prior to, during, or after use. Verification may be performed by measuring the frequency and amplitude of changes in the pacifier by a laser micrometer. In particular, the frequency and amplitude of the changes in the pacifier shape may be reviewed to verify that the desired therapy pulse is applied.

In addition, various aspects of the methods include providing summary remarks that may include data regarding a state of alertness for the patient.

The methods may also include steps for providing power to the non-nutritive suck application system, providing power to the non-nutritive suck appliance assembly, verifying a charge of a battery back-up unit, and logging in to the non-nutritive suck application. Further, the methods may have steps for adding a new patient to the displayed list of patients. Adding a new patient includes the steps of selecting an "add new patient" control button at the user interface, entering new patient data at the user interface, and, selecting a "save" control button to save the new patient data in the memory of the non-nutritive suck application.

In addition, at least one of the assessment session or the therapy protocol may be started by selecting a "start assessment" control button or a "start therapy" control button, respectively, at the user interface. Alternately, at least one of the assessment or the therapy protocol may be started by depressing a button on the orofacial stimulator appliance. Related objects and advantages of the present invention will be apparent from the following description.

DESCRIPTION OF FIGURES

FIG. 6 is a block diagram of an assessment module according to one aspect of the non-nutritive suck assessment and entrainment system.

FIG. 7 is a block diagram of a therapy module according to one aspect of the non-nutritive suck assessment and entrainment system.

FIG. 8A is a block diagram of a therapeutic pulse generation system according to one aspect of the non-nutritive suck assessment and entrainment system.

FIG. 8B is a block diagram of an orofacial stimulator appliance according to one aspect of the non-nutritive suck assessment and entrainment system.

FIG. 9 is a block diagram of a non-nutritive suck assessment and entrainment system according to one aspect.

FIGS. 12-31 are screenshots of various graphic user interface displays according to aspects of the non-nutritive suck assessment and entrainment system.

DETAILED DESCRIPTION OF THE INVENTION

The present invention relates to a system for assessing and the neural entrainment of a Non-Nutritive Suck (NNS) pattern in a patient. Typically, the patient is a premature infant; however, the system may also be used for patients unable to properly suck or swallow to receive nourishment, including but not limited to full-term infants, toddlers, adolescents, and adults. For example, the system may be used to treat those that have been debilitated by strokes, hemorrhages, or other conditions that correlate with an impairment in neurological development or function.

The NNS pattern of a patient is generated by the patient's suck central pattern generator (sCPG). A central pattern generator (CPGs) is a neural circuit or combination of neural circuits located in the patient's cerebral cortex, brainstem, and/or spinal cord that drives rhythmic motor behaviors such as sucking, breathing, mastication, and locomotion. The patterns generated by the CPGs can be modulated by a variety of external stimuli. As such, the most beneficial therapeutic results are manifested when the therapy consistently mimics the intrinsic frequency of sCPG.

It is often difficult for therapists to model the fine temporal structure of an organized NNS burst pattern, which involves a frequency-modulated (FM) burst structure, using manual stimulation. The FM burst structure is characterized by a series of suck cycles that successively decrease in frequency from the first compression cycle of the lips and mouth to the last compression cycle. The FM burst structure typically modulates between 1.5 Hz and 3 Hz. The structure of the FM burst is very difficult if not impossible to produce manually in a repeated pattern by even the most experienced therapist.

The present invention relates to the identification of particular characteristics of the FM burst structure and provides criteria or descriptions of features of the NNS pattern that may be used as diagnostic indicators for gauging the development of oromotor control among patients. Further, the identified characteristics may be useful in configuring a tactile stimulus that may be applied to patients to modify or correct a deficient NNS pattern.

The Non-nutritive Suck (NNS) Application System (NNS Application System)

Figure 1:
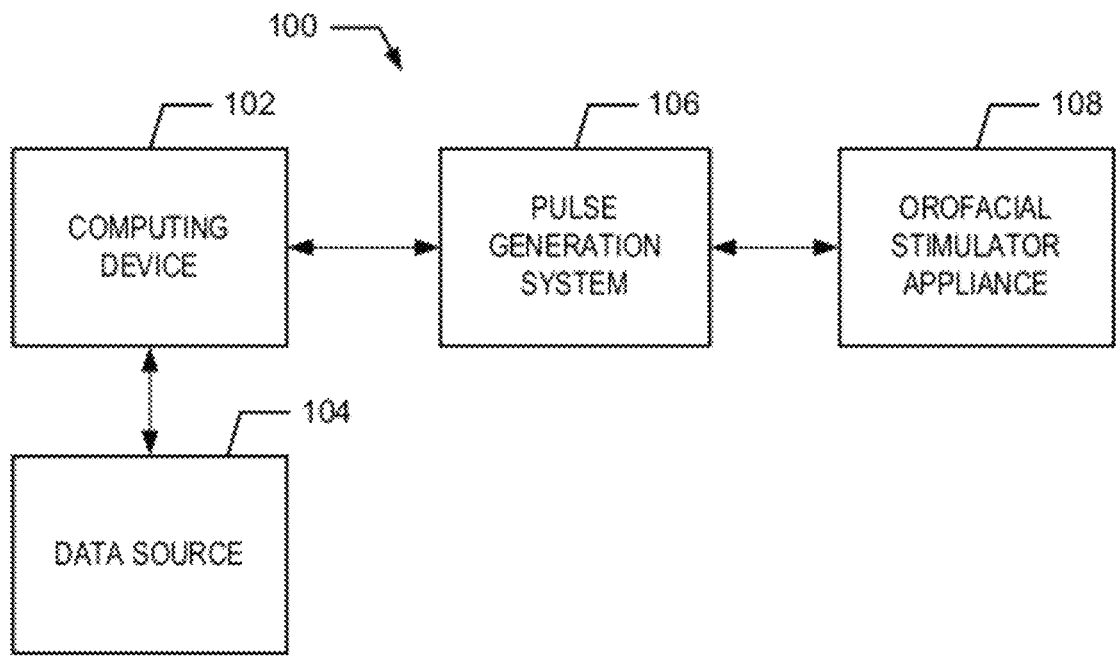
FIG. 1 is a block diagram of a non-nutritive suck assessment and entrainment system according to one aspect.

FIG. 1 is a block diagram of a non-nutritive suck (NNS) assessment and entrainment application system (NNS application system) 100 for assessing a patient's natural NNS pattern and for providing a tactile stimulus that will stimulate the suck central pulse generator (sCPG) and trigeminal nerve of a human brain to entrain a proper NNS pattern. Further, the NNS application system 100 may be used to assess and entrain brain activity for controlling respiration, mastication, or combinations thereof. The NNS application system 100 includes a computing device 102 to process data and execute one or more applications, a data source 104 to store data, a pulse generation system 106 to generate pneumatic pulses in response to input signals, and an orofacial stimulator appliance 108 to transfer the pneumatic pulses to a patient as a tactile stimulus.

Figure 2:
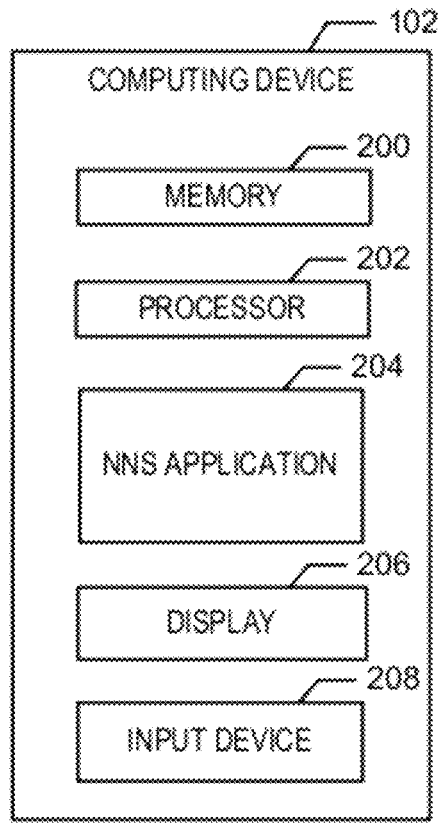
FIG. 2 is a block diagram of computing environment according to one aspect of the non-nutritive suck assessment and entrainment system.

According to one aspect, the computing device 102 includes memory 200 and at least one processor 202 to execute a NNS assessment and therapy application (NNS application) 204, as shown in FIG. 2. The computing device 102 also includes a display 206, such as a computer monitor, for displaying data stored in the data source 104, data received from the pulse generation system 106 or the orofacial stimulator appliance 108, and data input by a user of the NNS application system 100. The display device 206 also displays one or more graphical user interfaces (GUIs) input forms or displays, generated by the NNS application 204, as shown in FIGS. 12-31. The GUI input forms and displays enable a user of the NNS application system 100 to input, view, and/or interact with the various modules of the system. The GUI input forms and displays also allow a user to input, view, and/or interact with patient data, NNS assessment data, NNS therapy data, and/or other data related to the assessment and therapeutic stimulation of the patient. Further, the GUI input forms and displays permit a user to configure and interact with the pulse generation system 106 and the orofacial stimulator appliance 108.

The computing device 102 may also include an input device 208, such as a keyboard or a pointing device (e.g., a mouse, trackball, pen, or touch screen) to enter data or configure a feature of the NNS application system 100 using the GUI input forms and displays. The computing device 102 may further include, or at least be in communication with, the data source 104.

The data source 104 may be a database stored on a local hard disk drive (HDD) incorporated into the computing device 102. Alternately, the data source 104 may be a database or other data structure stored remotely from the computing device 102. For example, the computing device 102 may be in communication with the data source 104 over a network, including but not limited to the Internet. As shown in FIG. 7, the data source may store a variety of data. For example, the data source 104 may store user data 700 that includes profiles and login information, such as passwords, for users of the NNS application system 100. The data source 104 may also contain patient data 702 including patient charts and historical assessment and therapy session data 704 and 706, respectively. The data source 104 also stores data for therapy protocols or therapy pulse profiles 708 that may be used to entrain a variety of patients, as well as, other data 710 gathered from experiments or research trials conducted using the NNS application system 100.

Figure 3:
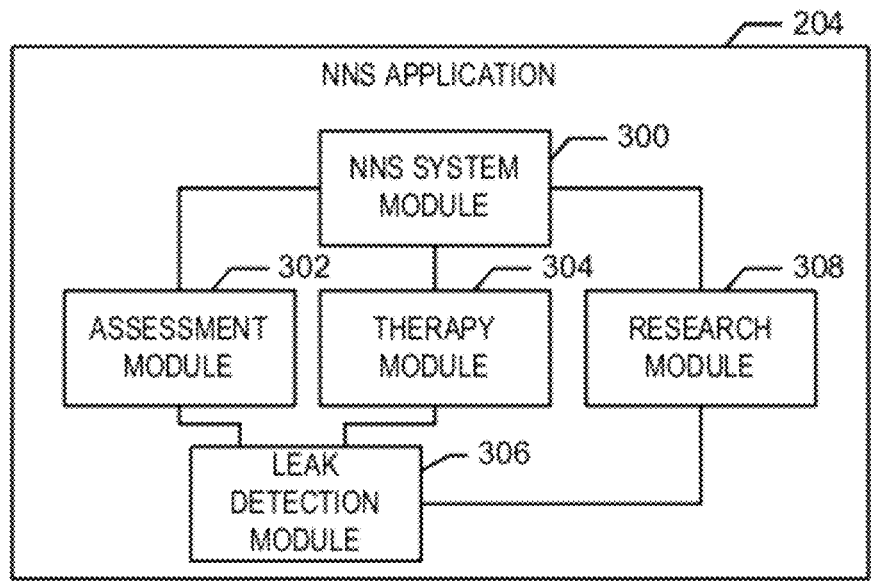
FIG. 3 is a block diagram of data source according to one aspect of the non-nutritive suck assessment and entrainment system.
Figure 4:
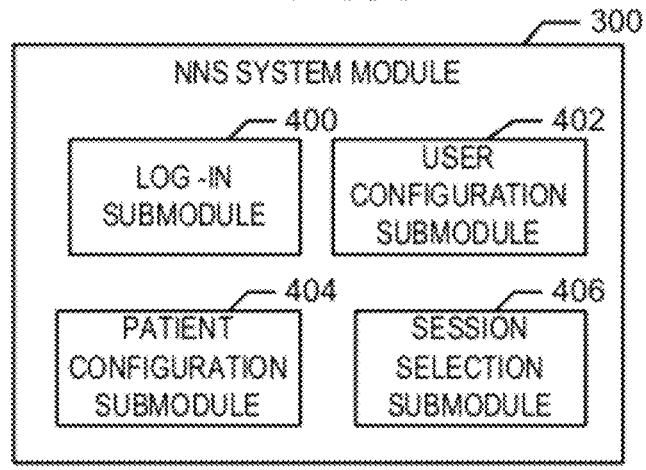
FIG. 4 is a block diagram of a non-nutritive suck entrainment application according to one aspect of the non-nutritive suck assessment and entrainment system.
Figure 5:
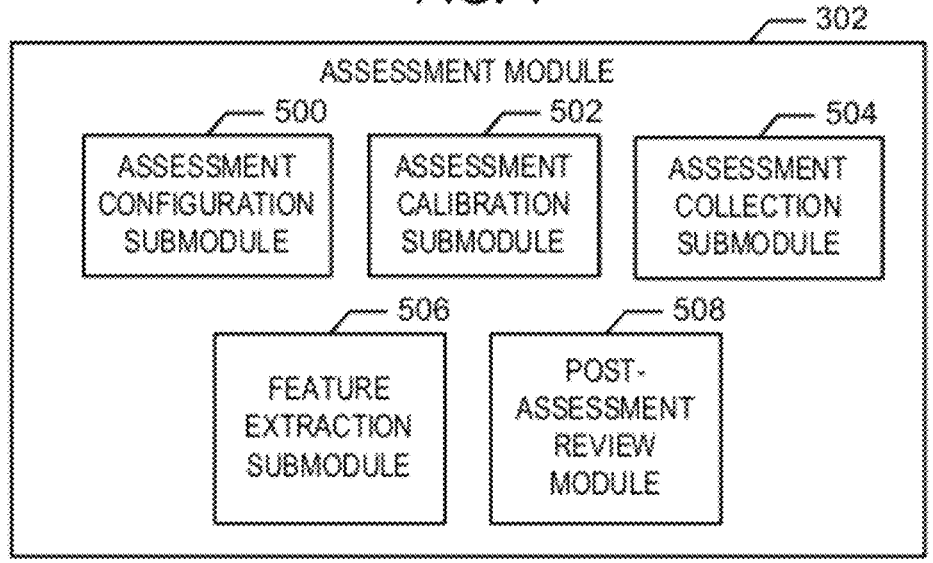
FIG. 5 is a block diagram of a system module according to one aspect of the non-nutritive suck assessment and entrainment system.

According to one aspect, as shown in FIG. 3, the NNS assessment and therapy application 204 includes a number of instructions, applets, modules 300-308, and submodules to receive, process, and generate data and/or signals for the assessment of a NNS pattern and the therapeutic stimulation of a patient's mouth and lips to entrain a proper NNS pattern. The modules of the NNS assessment and therapy application 204 include an NNS application system module 300, an assessment module 302, a therapy module 304, a leak detection module 306, and a research module 308.

Figure 12:
Figure 13:

The NNS application system module 300 includes various submodules 400-406 to provide access to various the features and functionality of the NNS assessment and therapy application 204. For example, the NNS application system module 300 includes a user login submodule 400 that allows a user of the NNS application system 100 to login into the NNS application 204. In one aspect, the NNS application system module 300 generates GUI input forms 1200 and 1202, as shown in FIGS. 12-13, where the user may select a user account and log in to the NNS application 204 after entering a valid password for the selected user.

Figure 14:
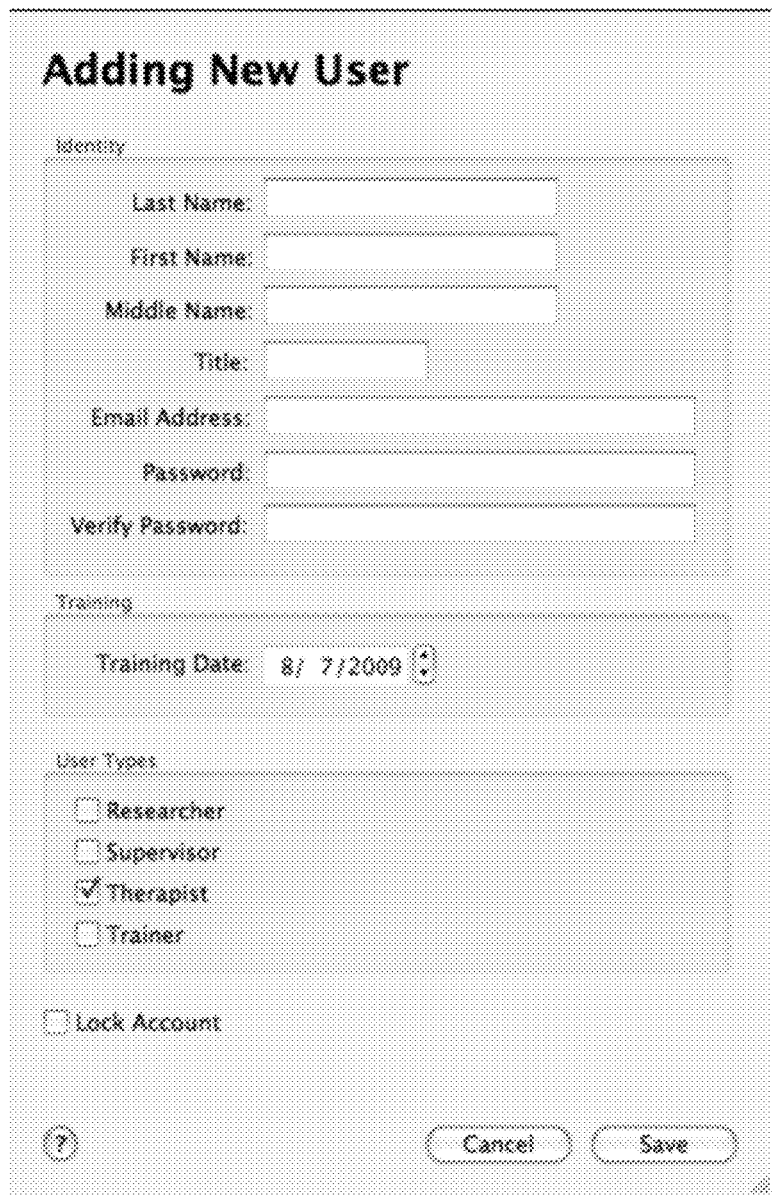
Figure 15:
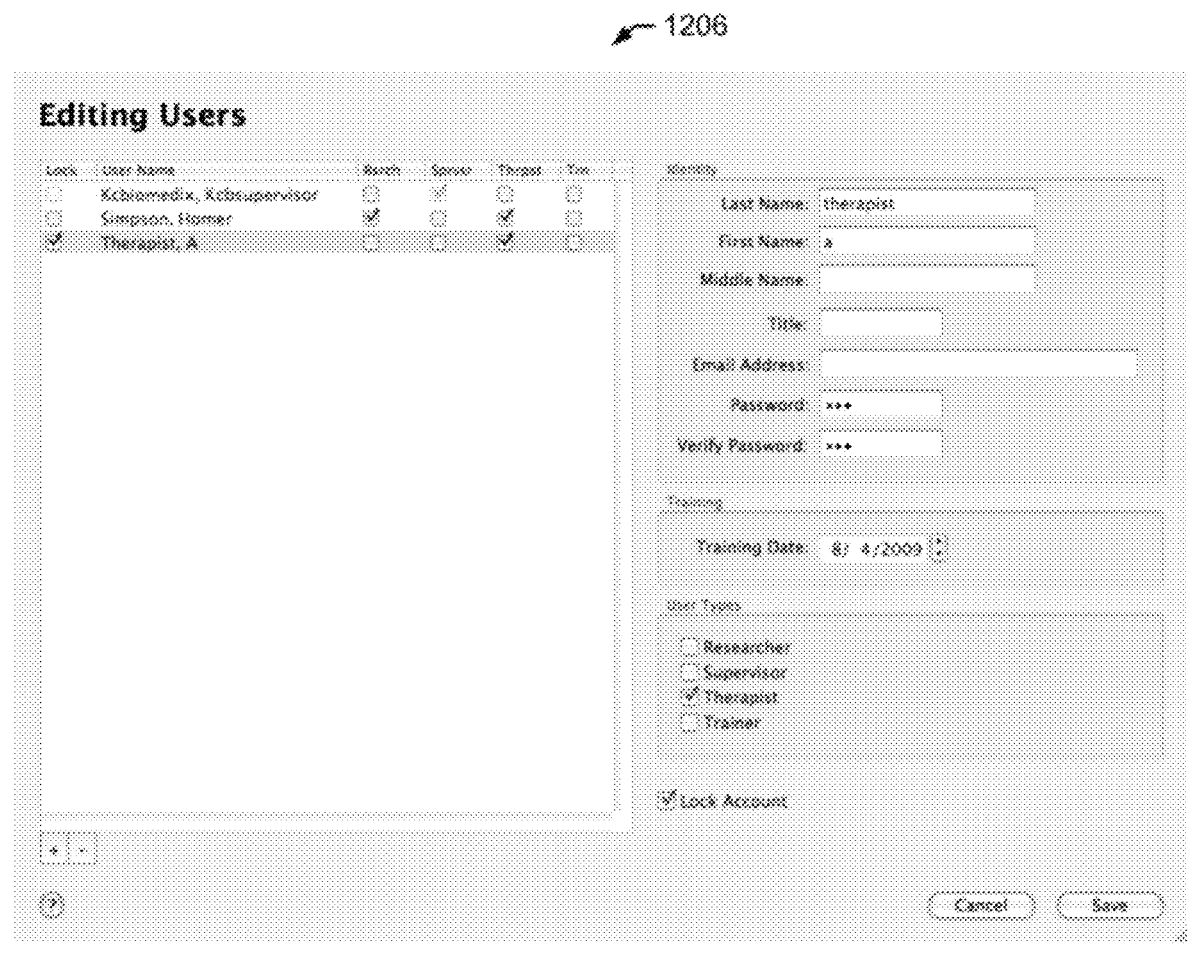

The NNS application system module 300 includes a user configuration submodule 402 that allows users of the NNS application system 100 with sufficient privileges to add, edit, or delete user accounts. By way of example and not limitation, an administrator may input data into GUI input forms 1204 and 1206, as shown in FIGS. 14-15 to create, modify, or delete a user profile to grant or restrict access to the NNS application 204.

Figure 17:
Figure 20:
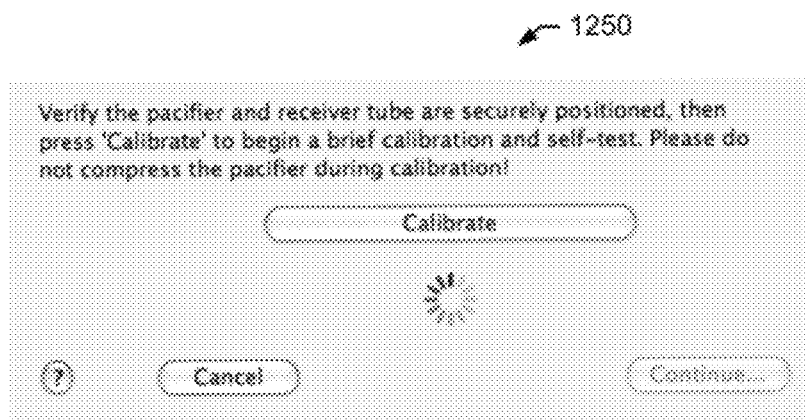
Figure 21:
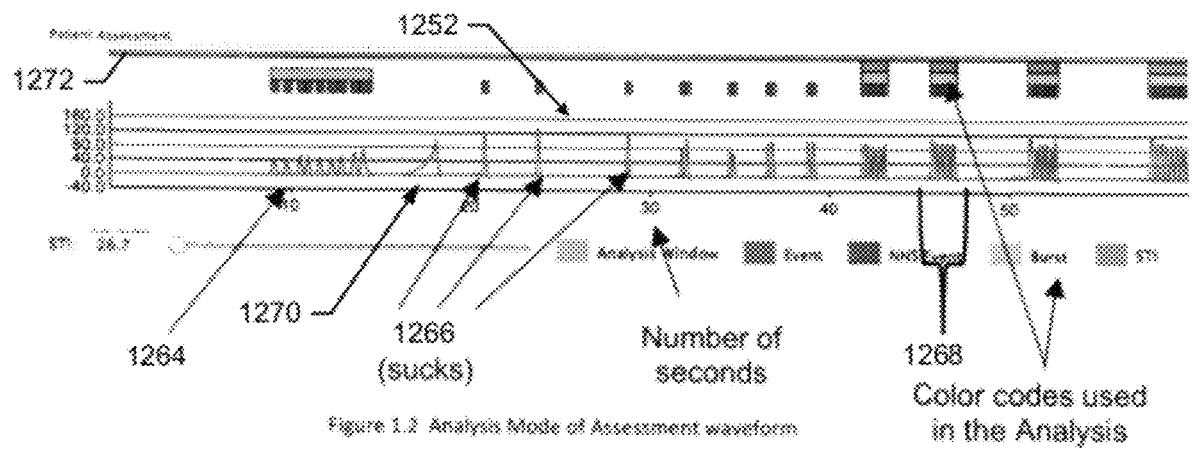
Figure 22:
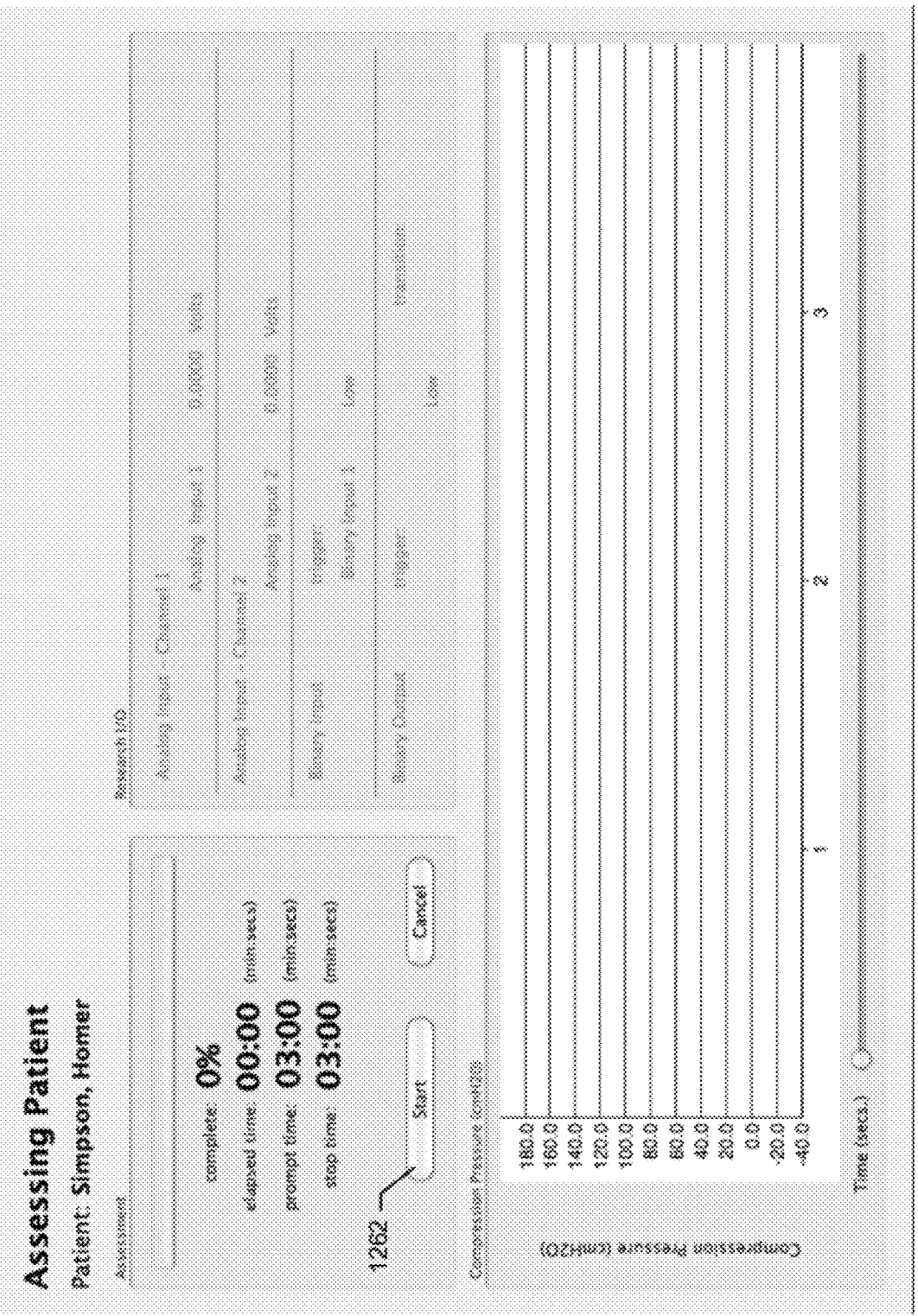
Figure 23:
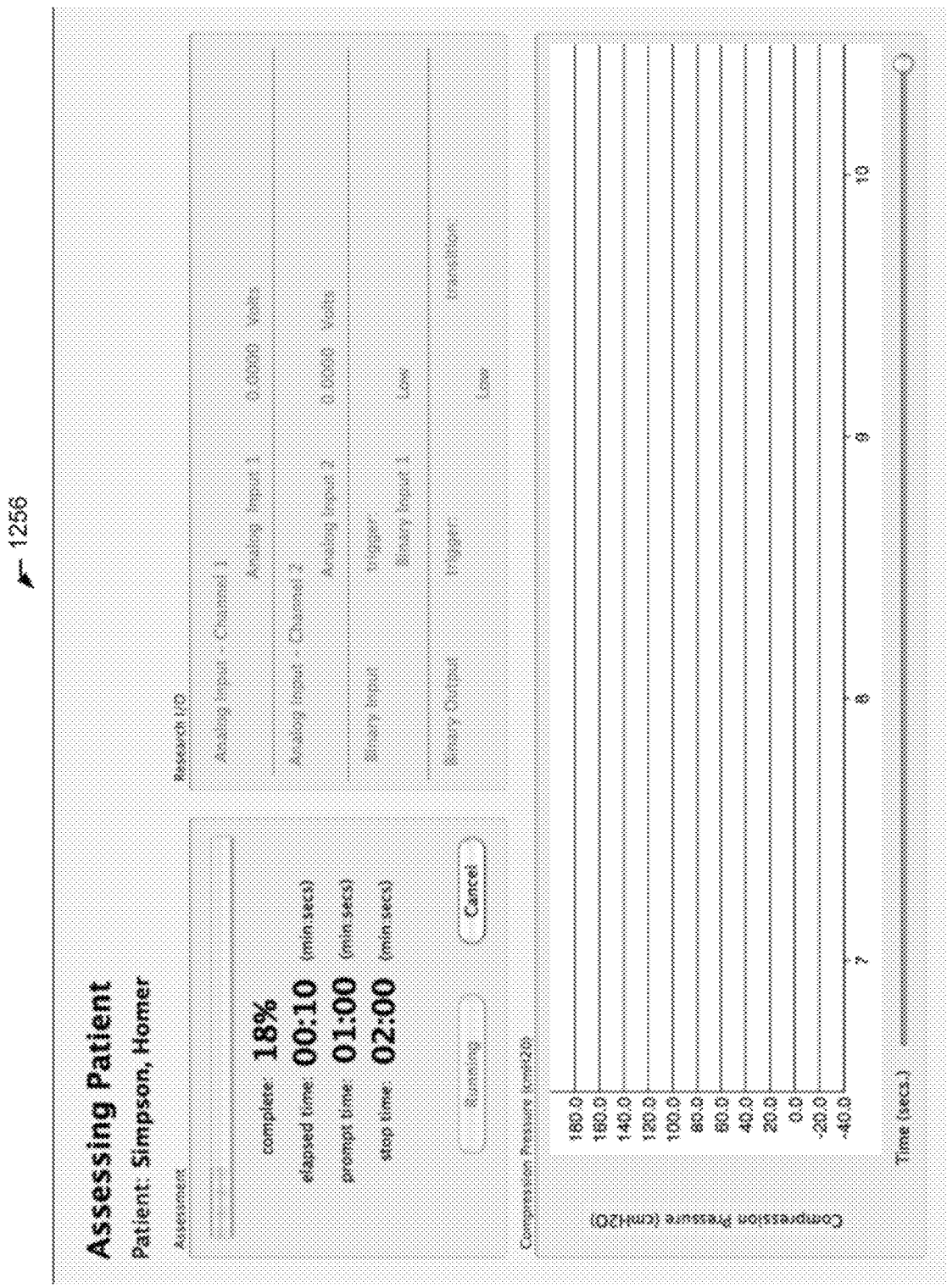
Figure 24:
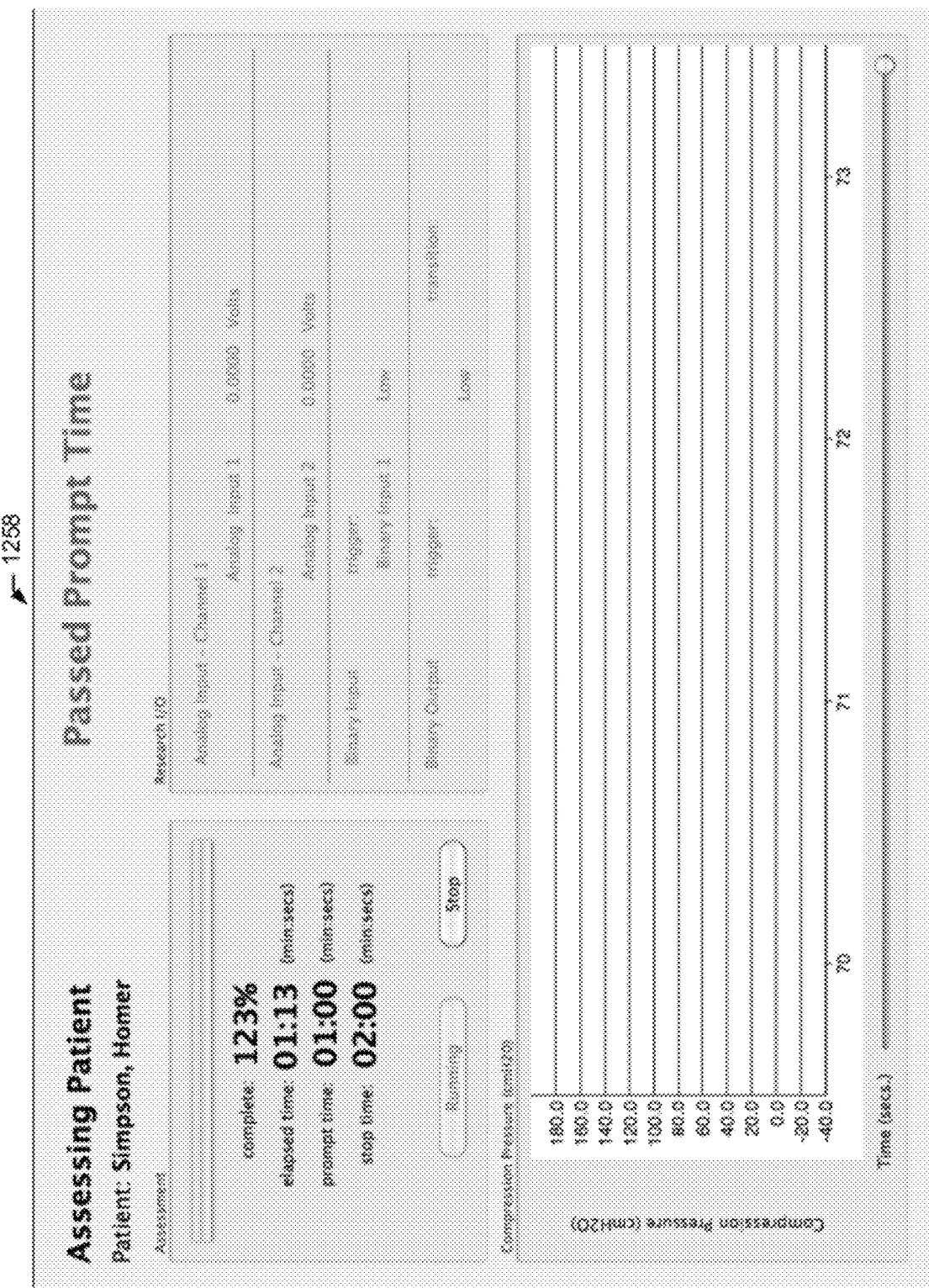
Figure 25:
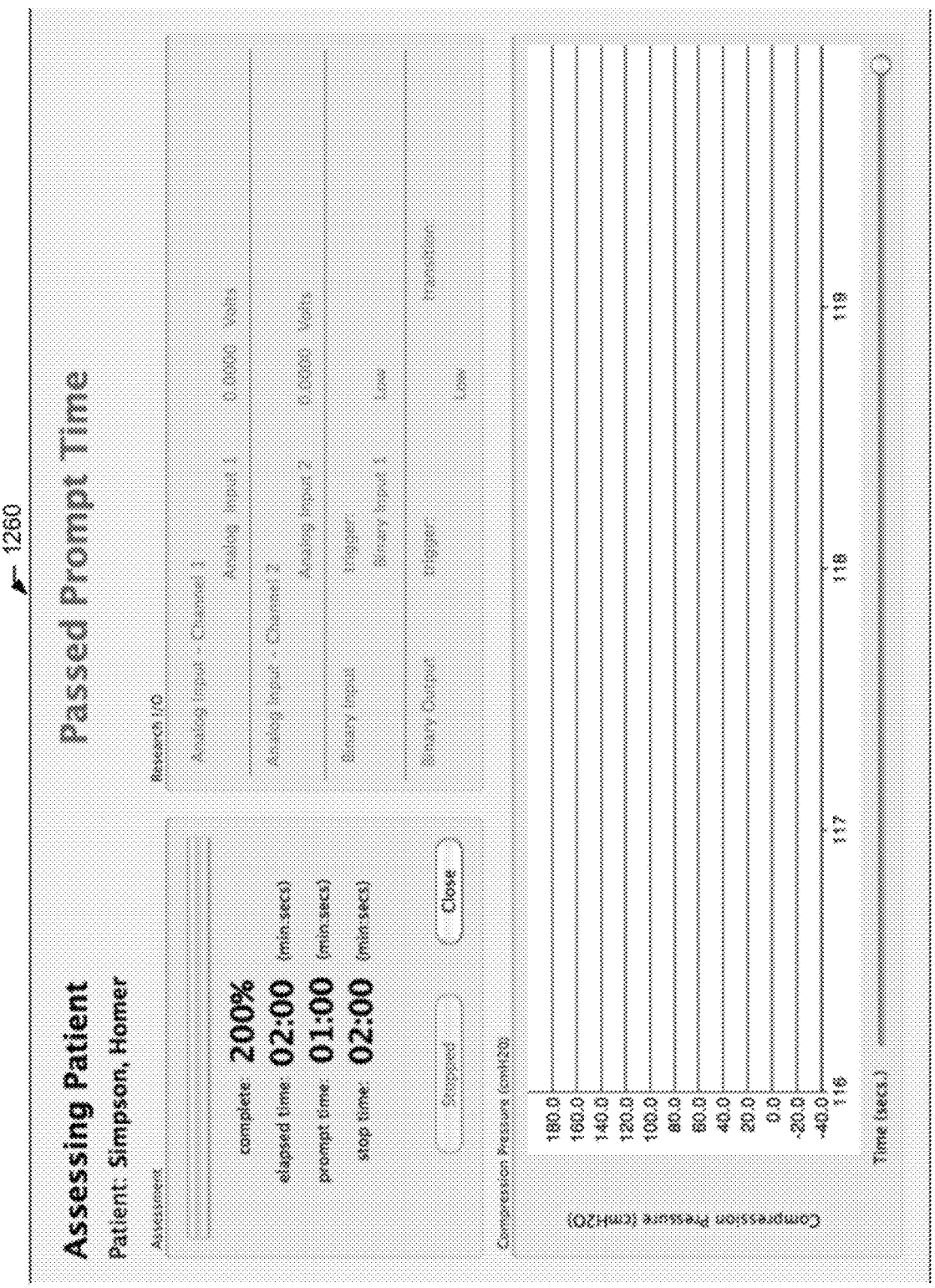

Similarly, the NNS application system module 300 includes a patient configuration submodule 404 that allows users of the NNS application system 100 with sufficient privileges to add, edit, or delete patients. By way of example and not limitation, an administrator may input data into input forms 1208 and 1210, as shown in FIGS. 16-17, to create, modify, or delete a profile for a patient that may receive an NNS assessment or therapy using the NNS application system 100. The NNS application system module 300 also includes a session selection submodule 406 that allows users of the NNS application system 100 to select whether the NNS application system will be used to assess a patient's naturally generated NNS pattern or to provide therapeutic stimulus to the patient. As such, the session selection submodule 406 sends requests to the assessment module 302 and the therapy module 404 in response to type of session selected by the user.

Figure 18:
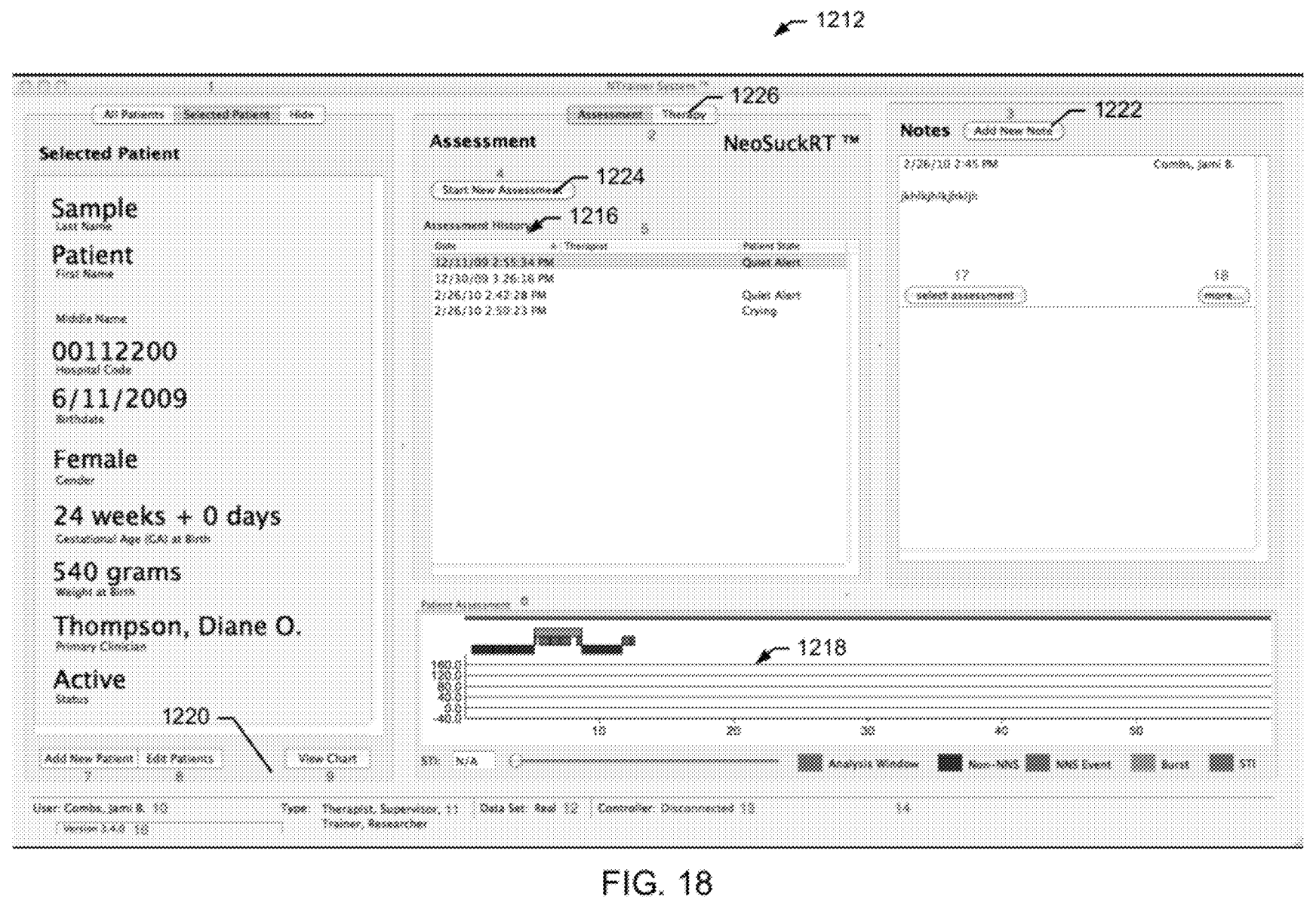

When an assessment request is generated, the NNS application system module 300 generates a main assessment input form 1212 to allow the user to input data and interact with the NNS application 204 during the assessment session. By way of example, and not limitation, an embodiment of the main assessment input form 1212 is shown in FIG. 18. In one aspect, the main assessment input form 1212 includes one or more control buttons 1214 to access a list of all the patients actively associated with the NNS application 204. When a patient is selected, the main assessment input form 1212 displays a history 1216 of assessments for the selected patient, and is capable of displaying waveforms from the previous assessments in a waveform frame 1218. In one aspect, the prior waveforms and assessment histories 1216 may be stored as assessment session data 704 in the data source 104.

Figure 31:
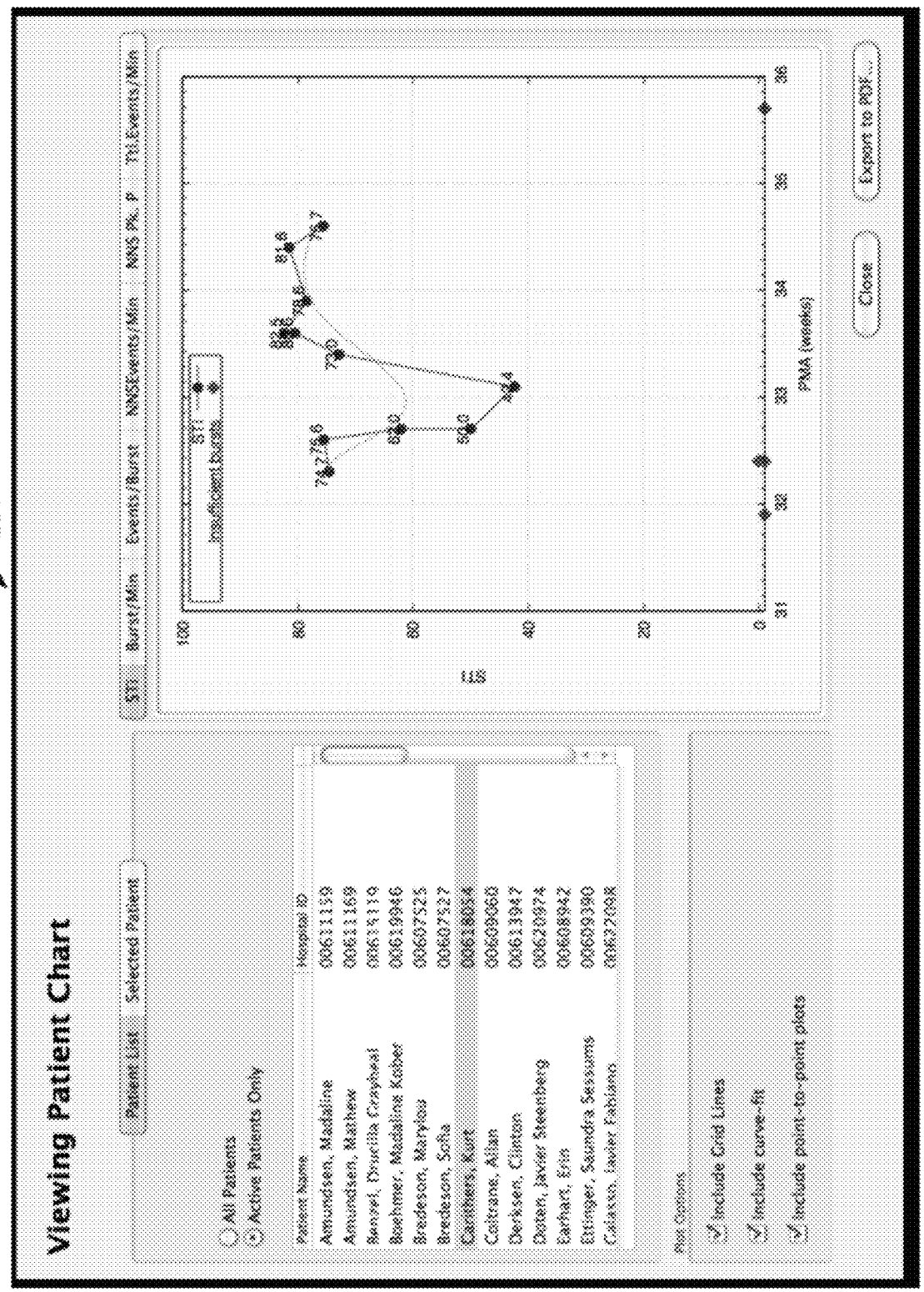

The main assessment input form 1212 also includes a control button 1220 to permit a user to view a patient's medical chart 1294, an example of which is shown in FIG. 31. In addition, the control button 1220 allows the user to add or edit patient data, while control button 1222 allows the user to add notes to the patient assessment data. In addition, the user may select control button 1224 to start a new assessment session for the selected patient or select control button 1226 to switch directly to a therapy session for the selected patient.

In one aspect, the assessment module 302 includes a number of submodules 500-508, including but not limited to an assessment configuration submodule 500, an assessment calibration submodule 502, an assessment capture module 504, a feature extraction submodule 506, and a post assessment review module 508. The various submodules 500-508 generate and display one or more GUI input forms as shown in FIGS. 19-26 that allow the user to configure, initiate, and review an assessment session.

The assessment configuration submodule 500, for example, generates an assessment configuration GUI input form 1228. The assessment configuration GUI input form 1228 includes one or more controls 1230-1242 and data fields 1244-1248 to input data for selecting or configuring an assessment session. The input data may relate to a total assessment time 1246, an intermediate assessment prompt 1244, a type and configuration 1236 of the pacifier 810, and optionally, the patient's weight 1248. As the behavior and mood of a patient is often unpredictable, it is difficult for the user to know in advance how long the assessment session may take. Therefore, the intermediate assessment prompt is selected as a 'best estimate' for the actual time that it may take to capture enough NNS pattern activity to assess the patient. As such, the total assessment time permits the user to continue to collect data, if desired, after the intermediate assessment prompt. In one aspect, the assessment collection submodule 504 halts the capture of assessment data at the intermediate assessment prompt.

The assessment calibration submodule 502 generates an assessment calibration GUI input form 1250. In one aspect, the calibration input form 1250 allows the user to communicate with and configure the pulse generation system 106 and the orofacial stimulator appliance 108 to verify the intended function and calibration for the components of the pulse generation system and the orofacial stimulator appliance prior to the initiation of an assessment session.

The assessment capture submodule 504 receives the digital pressure signal from the pulse generation system 106. In one aspect, the assessment capture submodule 504 records and displays the patient's NNS pattern activity as a waveform 1252. In other aspects, the assessment capture submodule 504 may receive and store the digital pressure signal without displaying the NNS pattern activity. In another aspect, the assessment capture submodule 504 may display the NNS pattern activity in another form, such as a chart, graph, or table.

The assessment capture submodule 504 may further generate a number of displays during the assessment capture session. For example, FIGS. 22-25 are screen displays that show the progress of the assessment session at the start of the session 1254, at the intermediate prompt interval 1256, at the user input duration time 1258, and at the conclusion of the assessment session 1260. In other aspects, fewer or a greater number of displays 1254-1260 may be provided during the assessment session.

In one aspect, the assessment data capture session may be initiated by input received through a start control button 1262 shown on the display 206. Alternately, the assessment data capture session may be initiated by a switch 816 on a handpiece 806 of the orofacial stimulator appliance 108.

During or subsequent to an assessment session, the feature extraction submodule 506 analyzes the digital pressure signal received by the assessment capture submodule 504. In particular, the feature extraction submodule 506 identifies various components of the patient's generated NNS pattern. For example, in the waveform 1252 of FIG. 21, the feature extraction submodule 506 identifies pressure peaks 1264, individual suck events 1266, as well as bursts 1268, which are defined as two or more suck events in less than about 1.2 seconds. In addition, the feature extraction submodule 506 also identifies a number of non-NNS events 1270, such as chewing motions made by the patient. In one aspect, the feature extraction submodule 506 may provide annotations, including color-coding, to identify the various NNS events 1264-1268.

In one aspect, the feature extraction submodule 506 quantifies the overall performance of the patient's generated NNS pattern by assigning a Spatiotemporal Index (STI) value to the pattern. For example, the STI value may be derived by calculating the similarity of up to five individual suck bursts. The STI value measures the symmetrical and repetition of the patient's generated NNS burst pattern by integrating the symmetry and quantity of selected NNS events 1264-1268 in the patient's NNS pattern.

In another aspect, the feature extraction submodule 506 automatically determines a number of parameters that are desirable for evaluating the patient's generated NNS pattern and determining the best course of therapy to treat the patient. For example, the evaluation parameters may include the STI value for the waveform, the number of bursts per minute, the number of events per burst, the number of NNS events per minute, an average peak pressure, as well as the total number of events per minute. In other examples, a fewer or greater number of parameters as well as different parameters may be considered when evaluating the patient's generated NNS pattern.

The evaluation parameters may be determined using a portion or subset of the collected assessment data. For example, a "most active" two-minute window having the most number of NNS events is identified by the feature extraction submodule 506. The most-active window is generally indicated by a bar 1272 on the displayed waveform 1252. When calculating the six evaluation parameters, the feature extraction submodule 506 may ignore any NNS activity outside of the most-active window.

After capturing the patient's generated NNS pattern and determining the evaluation parameters, the post assessment review module 508 generates a post-session GUI input form 1274 where the user may confirm the identify of the patient that underwent the assessment session and input notes regarding the assessment session. By way of example and not limitation, the user may indicate the state of alertness for the patient, by inputting terms such as alert, crying, drowsy, sleepy, or any other term that identifies the patient's level of alertness during the assessment session. The user may further quantify the patient's state of alertness as active or quiet, as the patient's STI value may fluctuate between assessment sessions due to the patient drifting off to sleep during the capture period.

Once a patient has been diagnosed or characterized as having a disorganized NNS pattern, it is often desirable for the patient to undergo a therapy session to entrain the patient's sCPG to produce an organized NNS pattern. Typically, a therapy session consists of applying an external stimulus to or near the lips and mouth of the patient in order to modify the NNS pattern generated by the sCPG. The orofacial stimulator appliance 108 contacts the patient on or near the lips and mouth to deliver therapeutic stimulation, provided by the pacifier's motion as caused by the pressure pulses, to the patient's orofacial nerves via regulated changes in the surface diameter of a pacifier 810 that is a component of the orofacial stimulator appliance 104, as shown in FIGS. 8B and 9. The pressure pulses conveyed by the orofacial stimulator appliance 108 are actuated at the pulse generator 104 system in response to a therapy pulse profile generated by the therapy module 304.

Figure 27:
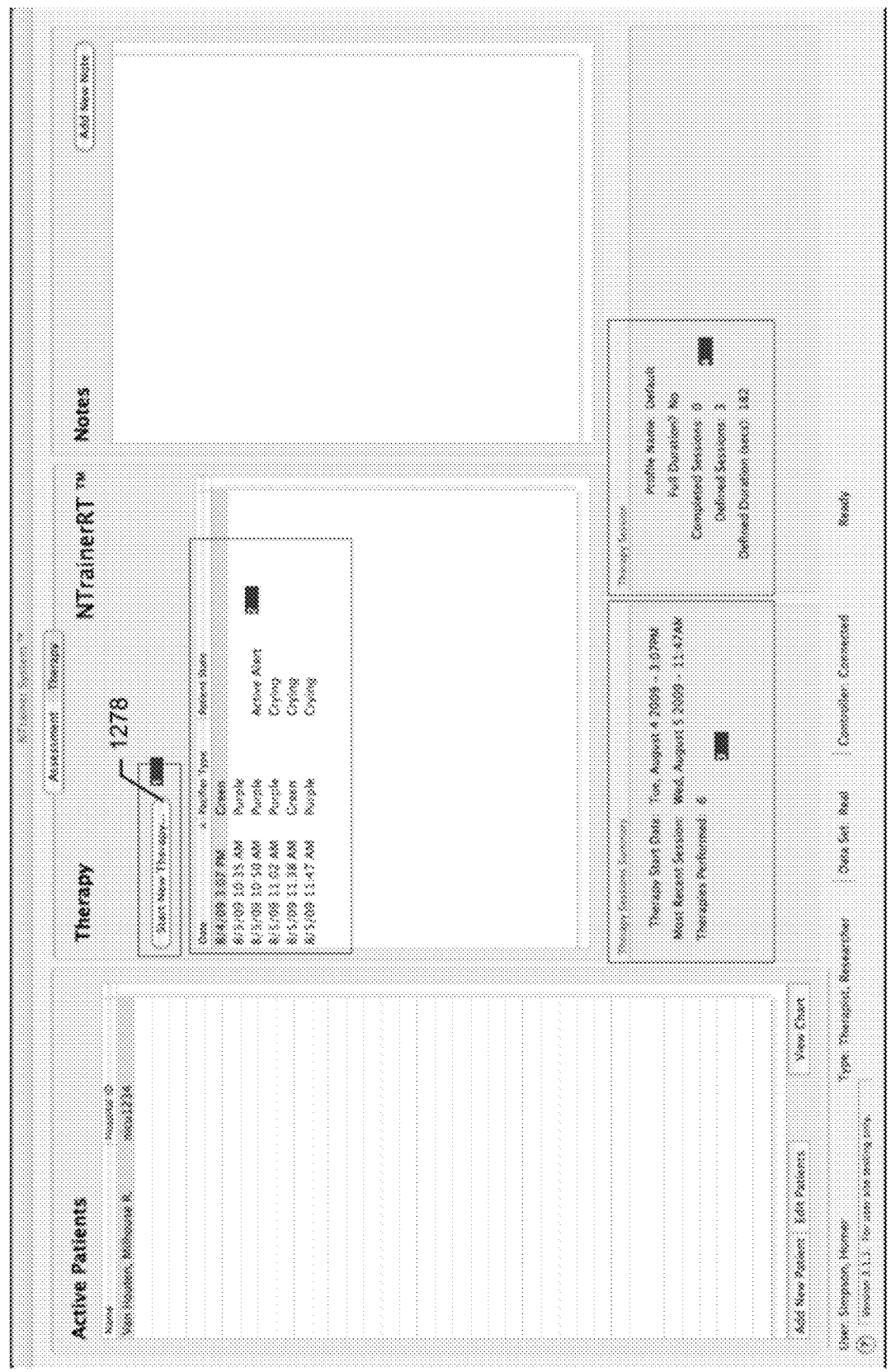
Figure 28:

When a therapy session is to be performed, the NNS application system module 300 generates a main therapy GUI input form 1276, as shown in FIG. 27. The main therapy GUI input form 1276 includes a control button 1278 to allow a user to start new therapy session. The main therapy GUI input form 1276 also includes a control button to display previous therapy session data 706 stored in the data source 104, the therapy sessions data 706 includes summaries and detailed information for previous therapy sessions.

In one aspect, the therapy module 304 includes a number of submodules 600-606, including but not limited to a therapy configuration submodule 600, a therapy calibration submodule 602, a therapy execution submodule 604, and a post-therapy review submodule 606. The various submodules 600-606 generate one or more GUI input forms for display that allow the user to configure, execute, and review a therapy session.

The therapy configuration submodule 600, for example, generates a therapy configuration input form 1280. The assessment configuration GUI input form 1280 includes a number controls 1282-1286 related to the therapy session and the pacifier 810 of the orofacial stimulator appliance 108. The assessment configuration GUI input form 1280 also includes a control button 1288 that allows the user to select or modify one or more therapy pulse profiles.

A therapy pulse profile consists of one or more therapeutic waveforms that result in variable but controlled radial displacements of the outer surface of the pacifier 810. The surface displacements of the pacifier 810 provide a tactile stimulus to or near the lips and mouth (e.g., intraoral, anterior tongue tip, anterior tongue dorsum) of the patient to entrain the patient's sCPG to naturally produce an NNS pattern that mimics the generated therapy waveforms. Once configured, the therapy waveforms are actuated by the pulse generation system 106, as shown in FIGS. 8A and 9.

The therapy calibration submodule 604 functions similar to the assessment calibration submodule 502 and generates a therapy calibration GUI input form similar to the assessment calibration GUI input form 1250. In one aspect, the calibration GUI input form allows the user to communicate with and configure the pulse generation system 106 and the orofacial stimulator appliance 108 to verify the intended function and calibration of the instruments prior to the start of the therapy session.

In one aspect, the expansion characteristics of the therapy pulses as delivered by expansion of the pacifier are verified using a laser micrometer (not shown) in communication with the therapy calibration submodule 604. The data from the laser micrometer regarding the frequency and amplitude components of the therapy pulse at the pacifier 810 may be digitized, recorded, and analyzed by the NNS application 204.

Figure 29:
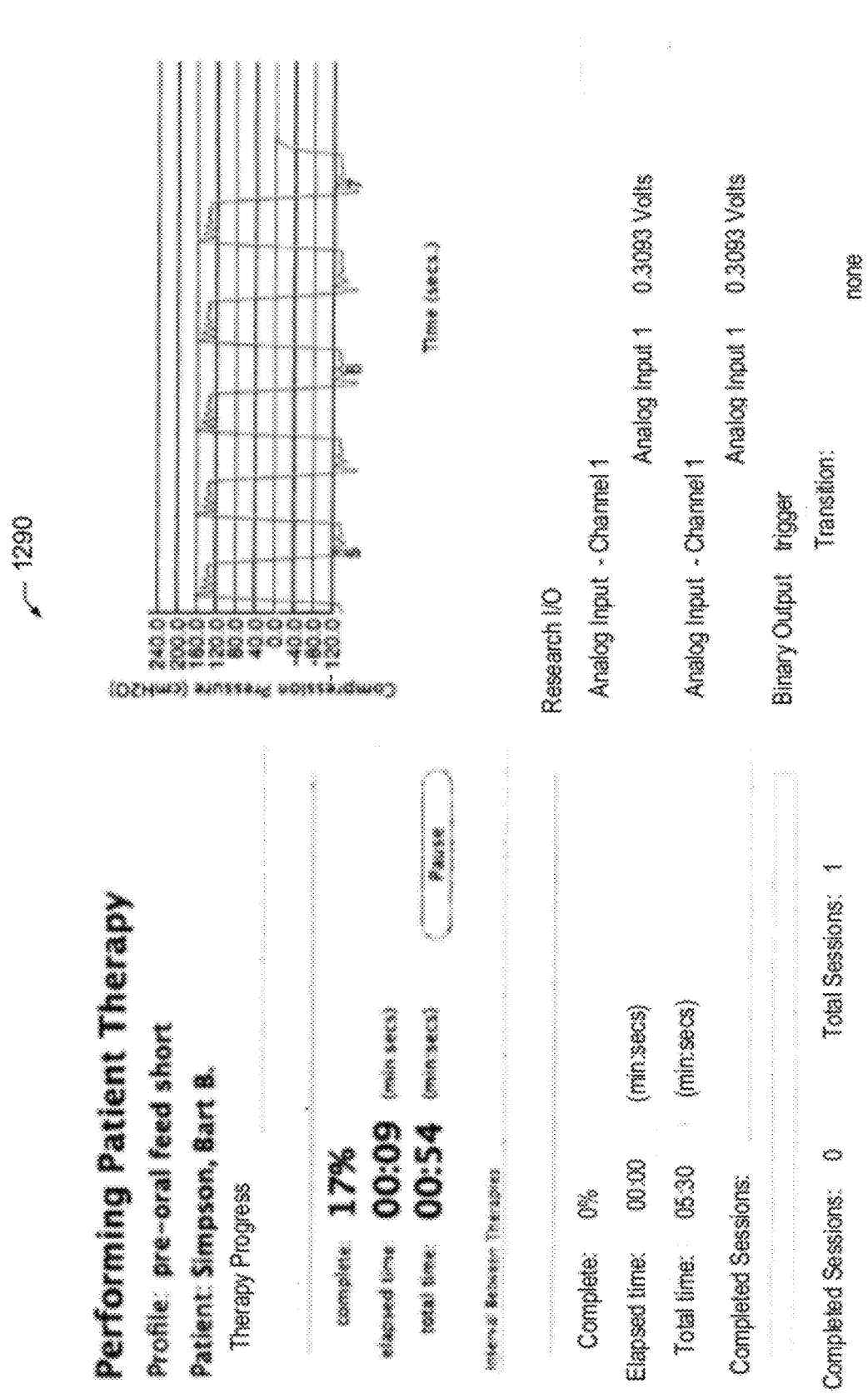

The therapy execution submodule 604 captures and displays the patient's NNS pattern activity during a therapy session. The therapy execution submodule 604 may generate a display 1290, as shown in FIG. 29, that shows progress of the therapy session at the start of the session, during the therapy session, at a rest interval, and at the conclusion of the therapy session, respectively. In other aspects, fewer or a greater number of displays may be provided during the therapy session.

Similar to an assessment session, the therapy session may be initiated by input received through the start control button 1278 of the GUI input form 1276. Alternately, the therapy session may be initiated by the switch 816 on a handpiece 806 of the orofacial stimulator appliance 108.

After a therapy session, the post-therapy review submodule 606 generates a post-session GUI input form similar to the assessment post session GUI input form 1274 where the user inputs notes regarding the therapy session. The user may indicate the state of alertness for the patient, such as alert, crying, drowsy, or sleepy.

The NNS application 204 further includes a leak detection module 306. The leak detection module 306 continuously monitors the performance of pneumatic subsystems within the pulse generator system 104 and the pneumatic lines and connections of the orofacial stimulator appliance 108 to detect air leaks.

Figure 30:
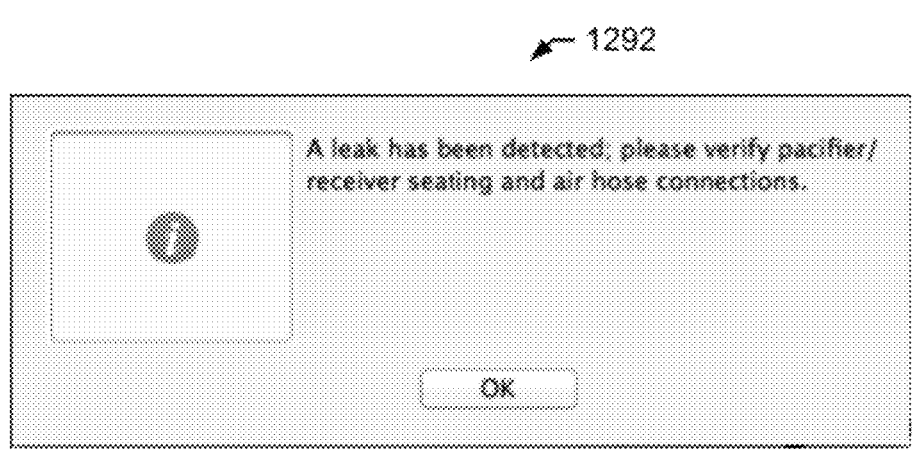

In one aspect, the leak detection module 306 determines that there may be an air leak by identifying reduced pulse amplitudes, increased pulse roll-offs, and/or the need for a greater stroke length in an air pump or a pneumatic pulse generator 804 to generate the requested pressure. Further, the leak detection module 306 can identify air leaks caused by disconnected air lines, and poorly seated receiver tubes or pacifiers. The module 306 will display a warning 1292, as shown in FIG. 30, requiring the user to address the leak. The leak detection module 306 may monitor the NNS application system 100 automatically and continuously during both assessment and therapy sessions.

The NNS application 204 also includes the research module 308 that allows a user of NNS application system 100 to conduct various research experiments and protocols. In particular, the research module 308 receives and transmits data to an input/output (I/O) port of the computing device 102 or the real-time controller 800 of the pulse generation system 106. The I/O port, in turn, may be in communication with any of a variety of external instruments for conducting research.

In various other aspects, the NNS application 204 may include additional modules for other functions, including those typically associated with medical or rehabilitation facilities. By way of example and not limitation, the NNS application 204 may also include a billing module to interface with an existing billing system or a printing module for printing various data, charts, or reports.

The NNS Therapeutic Appliance Assembly

Referring now to FIGS. 1, 8A-B, and 9, the NNS Therapeutic appliance assembly includes the pulse generation system 106 and the orofacial stimulator appliance 108. One or both of the pulse generation system 106 and the orofacial stimulator appliance 108 may be configured for each patient. By way of example, and not limitation, the size, shape, and/or type of pacifier 810 may be changed between patients.

The orofacial stimulator appliance 108 includes the handpiece 806 and the pacifier 810 that are brought into contact with the patient to deliver the therapeutic stimuli. In one aspect, the handpiece 806 includes a receiver tube 812 in fluid communication with the interior of the baglet or pacifier 810. The receiver tube 812 includes an interior void for receiving a volume of air from the pneumatic pulse generator 804 or from the pacifier 810. Optionally, the handpiece 806 also includes a receiver tube insert 814, that may be inserted in to the receiver tube 812 to limit the total volume of air in the interior void of receiver tube. The handpiece 806 may also include a mode valve 922 that is opened or closed depending on whether an assessment session or a therapy session is to be performed.

During an assessment session, the computing device 102 may record and display a signal received from a pressure transducer 808 of the orofacial stimulator appliance 108, as shown in FIG. 8B. The transducer 808 translates pressure changes caused by sucking and mouthing movements of the patient into an analog signal that tracks the pressure applied to a pacifier 810 versus time. The analog pressure signal is converted to a digital signal at an analog-to-digital converter 802 of the pulse generation system 106, as shown in FIG. 8A. The analog-to-digital converter 802 is incorporated into a real-time controller 800, that receives and modifies received and/or generated pressure signals in real-time. The digital pressure signal is then received, recorded, and displayed by the assessment module 302.

Similarly, in one aspect of a therapy session, the pulse generation system 106 receives amplitude data 900 and pulse duration data 902 for the desired waveforms. The amplitude data 900 and the pulse duration data are provided to the real-time controller 800 which may include an H-bridge (not shown) and a proportional—integral—derivative controller (PID controller) 904. By way of example and not limitation, the PID controller 904 may be a CompactRIO controller. The PID controller 904 generates a signal 906 that is fed through a pulse-width modulation (PWM) component 908. The modulated signal 910 is then provided to a motor 912 of the pneumatic pulse generator 804. In one embodiment, the pneumatic pulse generator 804 consists of a linear motor 912 mechanically engaged to an air cylinder, such as but not limited to an Airpel airpot or other device having a piston fitted in a precision bore cylinder with position and pressure feedback sensors in communication with the PID controller 904. The pulse generator 804 also includes a position feedback sensor 916 to monitor the position of the piston of the dashpot 914 and a pressure feedback sensor 918 to monitor the pressure with the dashpot 914. The air displaced by the pneumatic pulse generator 804 is then transmitted to the handpiece 806, through one or more pneumatic airlines, where the therapy waveform displaces the outer surface of the pacifier 810. The pulse generator 804 may also include a vent valve 920 that is normally closed, however the valve may be opened and vented to atmosphere to ensure pressure equilibrium at the start of each assessment or therapy session. Optionally, the pulse generator 804 may also include another valve (not shown) that isolates the dashpot 914 from the handpiece 806 during a Power-On Self Test (POST). The optional valve therefore permits diagnostic testing of the application system 100.

The Therapeutic Waveform

Preferably, the therapy waveform consists of one or more salient therapeutic bursts and each burst contains two or more square wave pulses. Typically, the bursts are separated by a configurable and variable delay interval.

According to one aspect, the nominal number of pulses in a desired therapeutic burst is six, while the actual number is configurable by users of the NNS application system 100. Preferably, each pulse in a therapeutic burst is a square wave pulse having the same configurable amplitude. Further, the period of each pulse increases sequentially thereby, causing the waveform frequency to slow down from the start of the therapeutic burst to the end of the therapeutic burst. A desirable decelerating sequence pulse sequence has periods of approximately 510±3 ms, 526±3 ms, 551±3 ms, 580±3 ms, and 626±3 ms between therapeutic bursts. When more than five pulses are used in the therapeutic burst, the sixth and all subsequent pulses have an periodic interval of approximately 626 ms.

Preferably, each square wave pulse period is shaped to minimize the positive and negative rise/fall times. For example, the transition intervals of each pulse's leading or trailing edges between each pulse may be tuned to create harmonics of 1.7±0.5 Hz, 5.5±0.5 Hz, 9.0±0.5 Hz, 12.5±0.5 Hz, and 16.5±0.5 Hz. It is desired that the therapy waveform have minimal ringing or flutter at the square wave peaks, in order to be perceived as a "clean" square waves. As the therapy pulse profiles may be modified in the amplitude and frequency domains, a power spectrum analysis shows that the preferred therapy waveform generates displacement of the pacifier 810 at a fundamental frequency of approximately 1.7 Hz and higher orders. This fundamental frequency is preferred to entrain the patient's nervous system through cutaneous signal detection. Further, the preferred therapy waveform has a Q factor greater than or equal to ½. As such, the relative high frequency of the rising and falling edges of the therapy pulse helps to achieve stimulus salience in the patient.

In all aspects, the number of square wave pulses per therapeutic burst, the number of therapeutic bursts per therapy session, and the amplitude of the square wave pulses are configurable by the user to account for variability in the patients. For example, the age, endurance, and/or aptitude of the patients may vary, thereby requiring the user to select or modify a therapy pulse profile via the therapy configuration submodule 600.

Methods of Using the Non-nutritive Suck Entrainment System (Entrainment System)

Figure 10:
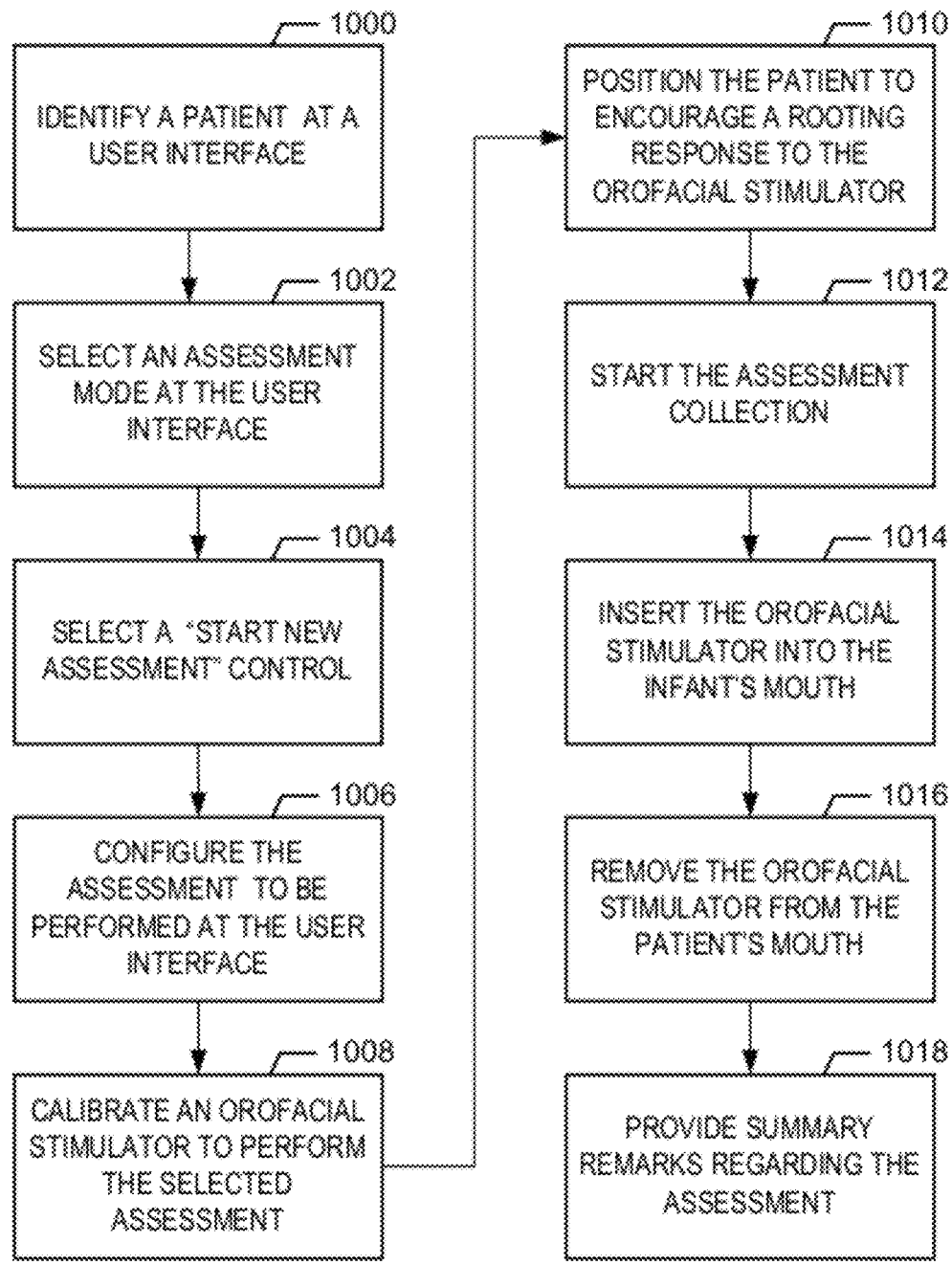
FIG. 10 illustrates a method for assessing a non-nutritive suck pattern according to one aspect of the non-nutritive suck assessment and entrainment system.

FIG. 10 illustrates a method for performing an assessment session to capture and analyze a patient's NNS pattern in accordance with an aspect of the NNS system 100. At step 1000, a user of the NNS system 100 selects a patient from a displayed list of patients. The user then selects a control button to enter the assessment mode of the NNS application 204 at step 1002 and selects the "start new assessment" control button 1224 at step 1004. The assessment session is configured as desired at step 1006 based upon the patient's age, injury, or other patient data 702 and optionally, data 704 regarding the patient's assessment history. The orofacial stimulator appliance 108 is calibrated at step 1008, while the patient is positioned to encourage a rooting response to the orofacial stimulator appliance at step 1010. At step 1012, the assessment session is started, while the orofacial stimulator appliance is contacted with the patient's lips and mouth at step 1014. In other aspects, the orofacial stimulator appliance 108 is inserted into the patient's mouth at step 1014. Similarly, in other aspects, the steps 1012 and 1014 may be reversed.

Once the assessment session is completed, the orofacial stimulator appliance 108 is removed from the patient at step 1016. After the feature extraction submodule 406 analyzes the collected assessment data, using the input form 1274 generated by the post-assessment review module 508. After the assessment session, the user may initiate another assessment session for the same patient or a different patient. Alternatively, the user may instead exit the NNS application 204.

Figure 11:
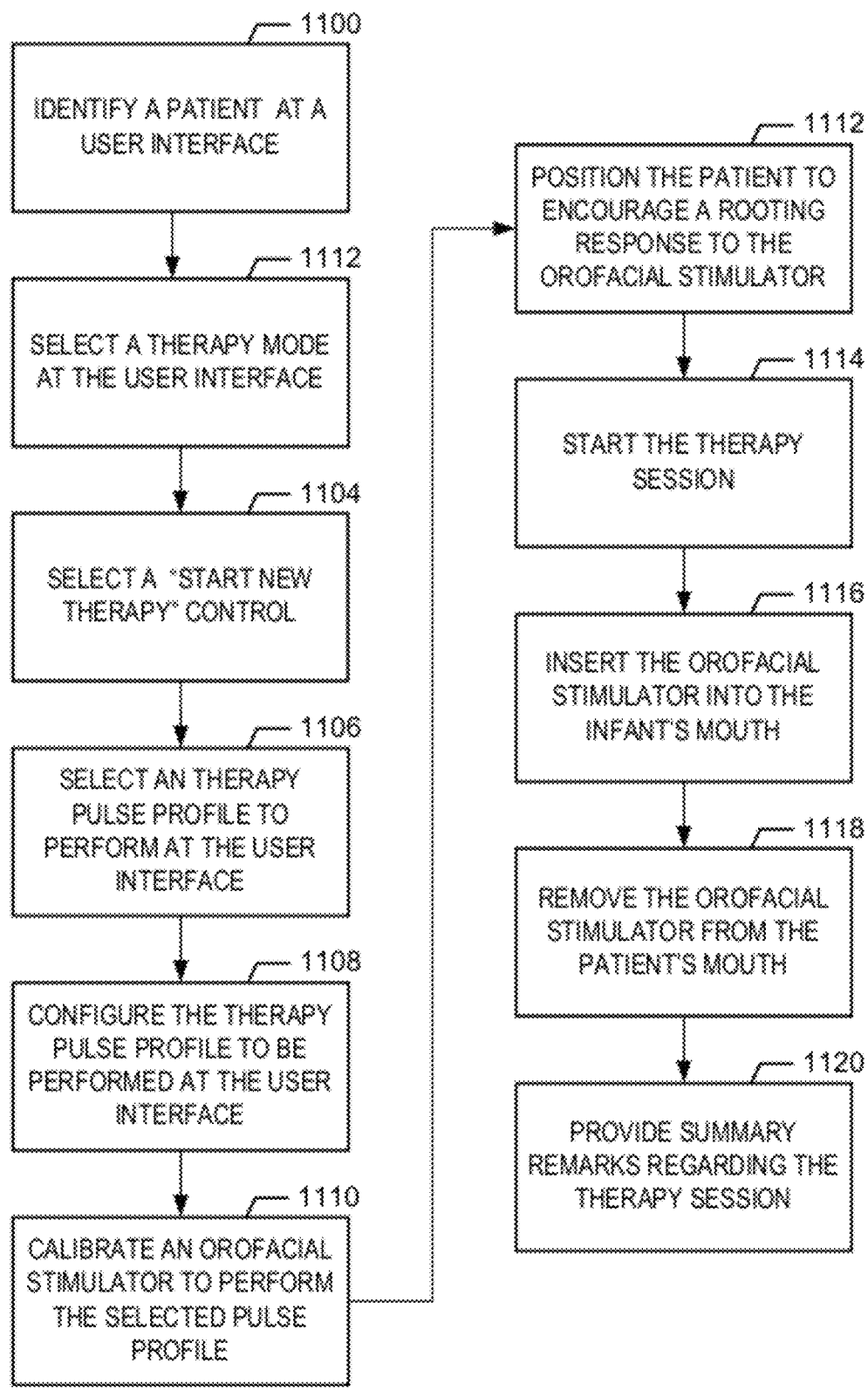
FIG. 11 illustrates a method for stimulating a patient to entrain an organized non-nutritive suck pattern according to one aspect of the non-nutritive suck assessment and entrainment system.

FIG. 11 illustrates a method for performing a therapy session to entrain a patient's sCPG to generate an organized NNS pattern in accordance with an aspect of the NNS application system 100. At step 1110, a user of the NNS application system 100 selects a patient from a list of patients. The user then selects a control button to enter the therapy mode of the NNS application 204 at step 1102 and the selects a "start new therapy" control button 1278 at step 1104. The therapy pulse profile to be generated during the therapy session is selected from the therapy pulse profile data 708 at step 1106 and at step 1108, the therapy pulse profile is configured as desired based upon the patient's age, injury, or other patient data 702 and any of the patients NNS assessment data 704. The orofacial stimulator appliance 108 is calibrated at step 1110, while the patient is positioned to encourage a rooting response to the orofacial stimulator appliance at step 1112. At step 1114, the therapy session is started, while the orofacial stimulator appliance is contacted with the patient's lips and mouth at step 1116. In other aspects, the orofacial stimulator appliance 108 is inserted into the patient's mouth at step 1116. Similarly, in other aspects, the steps 1114 and 1116 may be reversed. During the therapy session, the user may attempt to hold the patient as still as possible.

Once the therapy session is completed, the orofacial stimulator appliance 108 is removed from the patient at step 1118. The user may provide summary remarks regarding the therapy session at step 1120 using the GUI input form 1274 generated by the post-therapy review module 606. After the therapy session, the user may initiate another therapy session for the same patient or a different patient. Alternatively, the user may instead exit the NNS application 204.

Therapy sessions may be performed multiple times in the same day, week, or month. For example, a therapeutic session may consist of at least six pressure pulses in succession contacted with the patient for at least two minutes, at least twice a day. In other examples, a greater or fewer number of pressure pulses may be applied in succession or periodically.

It will be appreciated that the device and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore indicated by the appended claims rather than by the foregoing description. All changes, which come within the meaning and range of equivalency of the claims, are to be embraced within their scope.

What is claimed is:

1. A method for using a non-nutritive suck appliance assembly in communication with a non-nutritive suck application system to generate a productive non-nutritive suck pattern in a patient, the method comprising:

contacting the patient with the non-nutritive suck appliance assembly comprising an orofacial stimulator appliance, the orofacial stimulator appliance further comprising a pacifier, a receiver tube, and a receiver tube insert;

assessing a current non-nutritive suck pattern of the patient, wherein assessing the current non-nutritive suck pattern comprises:
at a user interface generated for display on a display device of the non-nutritive suck application system:
selecting the patient's name from a displayed list of patients generated by the non-nutritive suck application system, the non-nutritive suck application system having memory and executing a non-nutritive suck application on at least one processor;
selecting an assessment mode of the non-nutritive suck application;
selecting a displayed "new assessment" control button;
selecting an assessment session to be performed at the user interface; and,
configuring the assessment session at the user interface;
calibrating the orofacial stimulator appliance of the non-nutritive suck appliance assembly to perform the selected assessment session by inserting the receiver tube insert into the receiver tube of the orofacial stimulator appliance;
positioning the patient to encourage a rooting response to the orofacial stimulator appliance;
starting the assessment session;
inserting the orofacial stimulator appliance into the patient's mouth;
holding the orofacial stimulator appliance to maintain contact with the patient's mouth during the assessment session; and,
inputting summary remarks regarding the assessment session at the user interface;
receiving an assessment waveform by the non-nutritive suck application from the orofacial stimulator appliance, wherein a feature extraction step identifies at least one of a most active two minute period having the most NNS events, pressure peaks, suck events, bursts, or chewing motions, wherein the feature extraction quantifies the overall performance of the patient's current non-nutritive suck pattern by assigning a Spatiotemporal Index (STI) value to the pattern;
reviewing the assessment waveform;
determining if a therapy protocol is necessary to generate the productive non-nutritive suck pattern; and,
providing a therapeutic stimulus to the patient, wherein providing the therapeutic stimulus comprises:
at the user interface generated for display on the display device of the non-nutritive suck application system:
selecting the patient's name from the displayed list of patients;
selecting a therapy mode of the non-nutritive suck application;
selecting a displayed "new therapy" control button; and,
configuring a therapy protocol to be performed;
calibrating the orofacial stimulator appliance of the non-nutritive suck appliance assembly to perform the selected therapy protocol by adjusting the receiver tube insert in the receiver tube of the orofacial stimulator appliance to control a total volume of air in the receiver tube;

positioning the patient to encourage a rooting response to the orofacial stimulator appliance;

starting the selected therapy protocol, wherein a therapeutic waveform is administered having therapeutic bursts with a decelerating pulse sequence;

inserting the orofacial stimulator appliance into the patient's mouth;

holding the orofacial stimulator appliance to maintain contact with the patient's mouth during the therapy protocol; and, inputting summary remarks regarding the therapy protocol at the user interface.

2. The method of claim 1, wherein at least one of the assessment session or the therapy protocol is started by selecting a "start assessment" control button or a "start therapy" control button, respectively, at the user interface.

3. The method of claim 1, wherein calibrating the orofacial stimulator appliance to perform the assessment session further comprises actuating a-pneumatic valve on the orofacial stimulator appliance.

4. The method of claim 1, wherein the summary remarks comprise data regarding a state of alertness for the patient.

5. The method of claim 1 further comprising:
providing power to the non-nutritive suck application system;
providing power to the non-nutritive suck appliance assembly; and
logging in to the non-nutritive suck application.

6. The method of claim 1 further comprising:
adding a new patient to the displayed list of patients, wherein adding a new patient comprises:
entering new patient data at the user interface; and,
saving the new patient data in the memory of the non-nutritive suck application.

7. The method of claim 1, wherein calibrating the orofacial stimulator appliance to perform the selected therapy protocol further comprises actuating a pneumatic valve on the orofacial stimulator appliance.

8. The method of claim 1 further comprising measuring a frequency and an amplitude of at least one pacifier displacement.

9. The method of claim 1, wherein the step of holding the orofacial stimulator appliance to maintain contact with the patient's mouth during the therapy protocol further comprises:
at the non-nutritive suck application system, generating a therapeutic pressure pulse profile signal comprising a base frequency signal further comprising two or more pressure pulses, wherein each pressure pulse causes a displacement of a pacifier surface contacted by the lip and the mouth of the patient, wherein each of the two or more pressure pulses has a square wave profile and are separated by an interval between 500 milliseconds and 650 milliseconds in duration.

10. The method of claim 1, wherein the therapeutic pressure pulse profile signal comprises at least six pressure pulses in succession contacted with the patient for at least two minutes, at least twice a day.

11. The method of claim 1 wherein the STI value measures symmetry and repetition of the patient's current NNS pattern and is derived by integrating the symmetry and quantity of NNS events within the most active two minute period.

12. A method for using a non-nutritive suck appliance assembly in communication with a non-nutritive suck application system to generate a productive non-nutritive suck pattern in a patient, the method comprising:

contacting the patient with the non-nutritive suck appliance assembly comprising an orofacial stimulator appliance, the orofacial stimulator appliance further comprising a pacifier, a receiver tube, and a receiver tube insert;

assessing a current non-nutritive suck pattern of the patient, wherein assessing the current non-nutritive suck pattern comprises:
at a user interface generated for display on a display device of the non-nutritive suck application system:
selecting the patient's name from a displayed list of patients generated by the non-nutritive suck application system, the non-nutritive suck application system having memory and executing a non-nutritive suck application on at least one processor;
selecting an assessment mode of the non-nutritive suck application;
selecting a displayed "new assessment" control button;
selecting an assessment session to be performed at the user interface; and,
configuring the assessment session at the user interface;
calibrating the orofacial stimulator appliance of the non-nutritive suck appliance assembly to perform the selected assessment session by inserting the receiver tube insert into the receiver tube of the orofacial stimulator appliance;
positioning the patient to encourage a rooting response to the orofacial stimulator appliance;
starting the assessment session;
inserting the orofacial stimulator appliance into the patient's mouth;
holding the orofacial stimulator appliance to maintain contact with the patient's mouth during the assessment session; and,
inputting summary remarks regarding the assessment session at the user interface;

receiving an assessment waveform by the non-nutritive suck application from the orofacial stimulator appliance, wherein a feature extraction step identifies at least one of a most active two minute period having the most NNS events, pressure peaks, suck events, bursts, or chewing motions, wherein the feature extraction quantifies the overall performance of the patient's current non-nutritive suck pattern by assigning a Spatiotemporal Index (STI) value to the pattern;

reviewing the assessment waveform;

determining if a therapy protocol is necessary to generate the productive non-nutritive suck pattern; and, providing a therapeutic stimulus to the patient, wherein providing the therapeutic stimulus comprises:
at the user interface generated for display on the display device of the non-nutritive suck application system:
selecting the patient's name from the displayed list of patients;
selecting a therapy mode of the non-nutritive suck application;
selecting a displayed "new therapy" control button; and,
configuring a therapy protocol to be performed;
calibrating the orofacial stimulator appliance of the non-nutritive suck appliance assembly to perform the selected therapy protocol by adjusting the receiver tube insert in the receiver tube of the orofacial stimulator appliance to control a total volume of air in the receiver tube;

positioning the patient to encourage a rooting response to the orofacial stimulator appliance;

starting the selected therapy protocol, wherein a therapeutic waveform is administered having a square wave pulse period and transition intervals tuned to harmonic frequencies;

inserting the orofacial stimulator appliance into the patient's mouth;

holding the orofacial stimulator appliance to maintain contact with the patient's mouth during the therapy protocol; and, inputting summary remarks regarding the therapy protocol at the user interface.

\* \* \* \* \*